(12) United States Patent
Purcell et al.

(10) Patent No.: US 9,566,144 B2
(45) Date of Patent: Feb. 14, 2017

(54) VASCULAR FILTERS, DEFLECTORS, AND METHODS

(71) Applicant: CLARET MEDICAL, INC., Santa Rosa, CA (US)

(72) Inventors: Cameron Paul Purcell, Santa Rosa, CA (US); Daniel Wayne Fifer, Windsor, CA (US)

(73) Assignee: Claret Medical, Inc., Santa Clara, CA (US)

( * ) Notice: Subject to any disclaimer, the term of this patent is extended or adjusted under 35 U.S.C. 154(b) by 75 days.

(21) Appl. No.: 14/693,763

(22) Filed: Apr. 22, 2015

(65) Prior Publication Data

US 2016/0310255 A1    Oct. 27, 2016

(51) Int. Cl.
*A61F 2/24* (2006.01)
*A61F 2/01* (2006.01)

(52) U.S. Cl.
CPC .......... *A61F 2/013* (2013.01); *A61F 2002/016* (2013.01); *A61F 2230/0006* (2013.01); *A61F 2230/0015* (2013.01); *A61F 2230/0019* (2013.01); *A61F 2230/0067* (2013.01); *A61F 2250/006* (2013.01)

(58) Field of Classification Search
CPC ................ A61F 2/013; A61F 2002/011; A61F 2002/018; A61F 2230/0095; A61F 2/2427; A61F 2230/0093
USPC .................. 606/191, 194, 198, 200; 623/1.11
See application file for complete search history.

(56) References Cited

U.S. PATENT DOCUMENTS

| | | | |
|---|---|---|---|
| 3,472,230 A | 10/1969 | Fogarty | |
| 4,619,246 A | 10/1986 | Molgaard-Nielsen et al. | |
| 4,630,609 A | 12/1986 | Chin | |
| 4,650,466 A | 3/1987 | Luther | |
| 4,706,671 A | 11/1987 | Weinrib | |
| 4,723,549 A | 2/1988 | Wholey | |
| 4,873,978 A | 10/1989 | Ginsburg | |
| 5,108,419 A | 4/1992 | Reger | |
| 5,192,286 A | 3/1993 | Phan | |
| 5,200,248 A | 4/1993 | Thompson et al. | |
| 5,329,923 A | 7/1994 | Lundquist | |
| 5,348,545 A | 9/1994 | Shani et al. | |

(Continued)

FOREIGN PATENT DOCUMENTS

| | | |
|---|---|---|
| DE | 10049812 | 4/2002 |
| EP | 1400257 | 3/2004 |

(Continued)

OTHER PUBLICATIONS

Final Office Action for U.S. Appl. No. 13/338,914 dated Jul. 22, 2015, in 14 pages.

(Continued)

*Primary Examiner* — Katherine M Shi
(74) *Attorney, Agent, or Firm* — Knobbe Martens Olson & Bear, LLP

(57) ABSTRACT

Vascular filters and deflectors and methods for filtering bodily fluids. A blood filtering assembly can capture embolic material dislodged or generated during an endovascular procedure to inhibit or prevent the material from entering the cerebral vasculature. A blood deflecting assembly can deflect embolic material dislodged or generated during an endovascular procedure to inhibit or prevent the material from entering the cerebral vasculature.

20 Claims, 22 Drawing Sheets

(56) References Cited

U.S. PATENT DOCUMENTS

| | | |
|---|---|---|
| 5,381,782 A | 1/1995 | DeLaRama et al. |
| 5,395,327 A | 3/1995 | Lundquist et al. |
| 5,613,980 A | 3/1997 | Chauhan |
| 5,624,430 A | 4/1997 | Eton et al. |
| 5,662,671 A | 9/1997 | Barbut et al. |
| 5,707,389 A | 1/1998 | Louw et al. |
| 5,766,151 A | 6/1998 | Valley et al. |
| 5,779,716 A | 7/1998 | Cano et al. |
| 5,814,064 A | 9/1998 | Daniel |
| 5,827,324 A | 10/1998 | Cassell |
| 5,833,650 A | 11/1998 | Imran |
| 5,848,964 A | 12/1998 | Samuels |
| 5,897,529 A | 4/1999 | Ponzi |
| 5,897,819 A | 4/1999 | Miyata et al. |
| 5,910,154 A | 6/1999 | Tsugita et al. |
| 5,910,364 A | 6/1999 | Miyata et al. |
| 5,911,734 A | 6/1999 | Tsugita et al. |
| 5,935,139 A | 8/1999 | Bates |
| 5,980,555 A | 11/1999 | Barbut et al. |
| 5,989,281 A | 11/1999 | Barbut et al. |
| 5,993,469 A | 11/1999 | McKenzie et al. |
| 6,001,118 A | 12/1999 | Daniel |
| 6,010,522 A | 1/2000 | Barbut et al. |
| 6,027,520 A | 2/2000 | Tsugita et al. |
| 6,042,598 A | 3/2000 | Tsugita et al. |
| 6,045,547 A | 4/2000 | Ren et al. |
| 6,051,014 A | 4/2000 | Jang |
| 6,080,140 A | 6/2000 | Swaminathan et al. |
| 6,083,239 A | 7/2000 | Addis |
| 6,096,053 A | 8/2000 | Bates |
| 6,099,534 A | 8/2000 | Bates |
| 6,120,494 A | 9/2000 | Jonkman |
| 6,126,673 A | 10/2000 | Kim et al. |
| 6,142,987 A | 11/2000 | Tsugita |
| 6,146,396 A | 11/2000 | Konya et al. |
| 6,152,946 A | 11/2000 | Broome et al. |
| 6,171,328 B1 | 1/2001 | Addis |
| 6,179,851 B1 | 1/2001 | Barbut et al. |
| 6,235,045 B1 | 5/2001 | Barbut et al. |
| 6,245,087 B1 | 6/2001 | Addis |
| 6,245,088 B1 | 6/2001 | Lowery |
| 6,245,089 B1 | 6/2001 | Daniel |
| 6,264,663 B1 | 7/2001 | Cano |
| 6,270,513 B1 | 8/2001 | Tsugita et al. |
| 6,277,138 B1 | 8/2001 | Levinson et al. |
| 6,287,321 B1 | 9/2001 | Jang |
| 6,290,710 B1 | 9/2001 | Cryer et al. |
| 6,309,399 B1 | 10/2001 | Barbut et al. |
| 6,325,815 B1 | 12/2001 | Kusleika |
| 6,336,934 B1 | 1/2002 | Gilson et al. |
| 6,346,116 B1 | 2/2002 | Brooks et al. |
| 6,361,545 B1 | 3/2002 | Macoviak et al. |
| 6,364,900 B1 | 4/2002 | Heuser |
| 6,371,971 B1 | 4/2002 | Tsugita et al. |
| 6,375,628 B1 | 4/2002 | Zadno-Azizi et al. |
| 6,383,174 B1 | 5/2002 | Eder |
| 6,383,205 B1 | 5/2002 | Samson et al. |
| 6,440,120 B1 | 8/2002 | Maahs |
| 6,454,799 B1 | 9/2002 | Schreck |
| 6,485,502 B2 | 11/2002 | Don Michael |
| 6,499,487 B1 | 12/2002 | McKenzie et al. |
| 6,517,559 B1 | 2/2003 | O'Connell |
| 6,537,297 B2 | 3/2003 | Tsugita et al. |
| 6,558,356 B2 | 5/2003 | Barbut |
| 6,595,983 B2 | 7/2003 | Voda |
| 6,605,102 B1 | 8/2003 | Mazzocchi |
| 6,620,148 B1 | 9/2003 | Tsugita |
| 6,648,837 B2 | 11/2003 | Kato et al. |
| 6,663,652 B2 | 12/2003 | Daniel et al. |
| 6,676,682 B1 | 1/2004 | Tsugita et al. |
| 6,712,834 B2 | 3/2004 | Yassour et al. |
| 6,712,835 B2 | 3/2004 | Mazzocchi |
| 6,719,717 B1 | 4/2004 | Johnson et al. |
| 6,726,621 B2 | 4/2004 | Suon et al. |
| 6,726,651 B1 | 4/2004 | Robinson et al. |
| 6,726,701 B2 | 4/2004 | Gilson |
| 6,740,061 B1 | 5/2004 | Oslund |
| 6,817,999 B2 | 11/2004 | Berube et al. |
| 6,830,579 B2 | 12/2004 | Barbut |
| 6,843,798 B2 | 1/2005 | Kusleika et al. |
| 6,872,216 B2 | 3/2005 | Daniel |
| 6,881,194 B2 | 4/2005 | Miyata et al. |
| 6,887,258 B2 | 5/2005 | Denison et al. |
| 6,905,490 B2 | 6/2005 | Parodi |
| 6,907,298 B2 | 6/2005 | Smits et al. |
| 6,958,074 B2 | 10/2005 | Russell |
| 6,969,396 B2 | 11/2005 | Krolik et al. |
| 7,011,094 B2 | 3/2006 | Rapacki et al. |
| 7,048,752 B2 | 5/2006 | Mazzocchi |
| 7,094,249 B1 | 8/2006 | Broome |
| 7,115,134 B2 | 10/2006 | Chambers |
| 7,160,255 B2 | 1/2007 | Saadat |
| 7,169,161 B2 | 1/2007 | Bonnette et al. |
| 7,169,165 B2 | 1/2007 | Belef et al. |
| 7,182,757 B2 | 2/2007 | Miyata et al. |
| 7,214,237 B2 | 5/2007 | Don Michael |
| 7,278,974 B2 | 10/2007 | Kato et al. |
| 7,303,575 B2 | 12/2007 | Ogle |
| 7,313,445 B2 | 12/2007 | McVenes et al. |
| 7,323,001 B2 | 1/2008 | Clubb et al. |
| 7,329,278 B2 | 2/2008 | Seguin et al. |
| 7,399,308 B2 | 7/2008 | Borillo et al. |
| 7,410,491 B2 | 8/2008 | Hopkins |
| 7,493,154 B2 | 2/2009 | Bonner et al. |
| 7,559,925 B2 | 7/2009 | Goldfarb et al. |
| 7,572,272 B2 | 8/2009 | Denison et al. |
| 7,621,904 B2 | 11/2009 | McFerran et al. |
| 7,766,961 B2 | 8/2010 | Patel et al. |
| 7,918,859 B2 | 4/2011 | Katoh et al. |
| 7,922,732 B2 | 4/2011 | Mazzocchi et al. |
| 7,998,104 B2 | 8/2011 | Chang |
| 8,002,790 B2 | 8/2011 | Brady et al. |
| 8,021,351 B2 | 9/2011 | Boldenow et al. |
| 8,092,483 B2 | 1/2012 | Galdonik et al. |
| 8,372,108 B2 | 2/2013 | Lashinski |
| 8,382,788 B2 | 2/2013 | Galdonik |
| 8,518,073 B2 | 8/2013 | Lashinski |
| 8,753,370 B2 | 6/2014 | Lashinski |
| 8,876,796 B2 | 11/2014 | Fifer et al. |
| 8,974,489 B2 | 3/2015 | Lashinski |
| 9,017,364 B2 | 4/2015 | Fifer et al. |
| 9,055,997 B2 | 6/2015 | Fifer et al. |
| 9,259,306 B2 | 2/2016 | Fifer et al. |
| 9,326,843 B2 | 5/2016 | Lee et al. |
| 9,345,565 B2 | 5/2016 | Fifer et al. |
| 2001/0041858 A1 | 11/2001 | Ray et al. |
| 2002/0022858 A1 | 2/2002 | Demond et al. |
| 2002/0026145 A1 | 2/2002 | Bagaoisan et al. |
| 2002/0055767 A1 | 5/2002 | Forde et al. |
| 2002/0068015 A1 | 6/2002 | Polaschegg et al. |
| 2002/0077596 A1 | 6/2002 | McKenzie et al. |
| 2002/0095170 A1 | 7/2002 | Krolik et al. |
| 2002/0095172 A1 | 7/2002 | Mazzocchi et al. |
| 2002/0123761 A1 | 9/2002 | Barbut et al. |
| 2002/0161394 A1 | 10/2002 | Macoviak et al. |
| 2002/0165571 A1 | 11/2002 | Hebert et al. |
| 2002/0165573 A1 | 11/2002 | Barbut |
| 2003/0100919 A1 | 5/2003 | Hopkins et al. |
| 2003/0130684 A1 | 7/2003 | Brady et al. |
| 2003/0144686 A1 | 7/2003 | Martinez et al. |
| 2003/0171770 A1 | 9/2003 | Kusleika et al. |
| 2003/0199960 A1 | 10/2003 | Paskar |
| 2004/0002730 A1 | 1/2004 | Denison et al. |
| 2004/0006370 A1 | 1/2004 | Tsugita |
| 2004/0044350 A1 | 3/2004 | Martin et al. |
| 2004/0044360 A1 | 3/2004 | Lowe |
| 2004/0064092 A1 | 4/2004 | Tsugita et al. |
| 2004/0093015 A1 | 5/2004 | Ogle |
| 2004/0167565 A1 | 8/2004 | Beulke et al. |
| 2004/0193206 A1 | 9/2004 | Gerberding |
| 2004/0215167 A1 | 10/2004 | Belson |
| 2004/0220611 A1 | 11/2004 | Ogle |
| 2004/0225321 A1 | 11/2004 | Krolik et al. |
| 2004/0230220 A1 | 11/2004 | Osborne |

(56) References Cited

U.S. PATENT DOCUMENTS

| | | |
|---|---|---|
| 2004/0243175 A1 | 12/2004 | Don Michael |
| 2004/0254601 A1 | 12/2004 | Eskuri |
| 2004/0254602 A1 | 12/2004 | Lehe et al. |
| 2005/0010285 A1 | 1/2005 | Lambrecht et al. |
| 2005/0065397 A1 | 3/2005 | Saadat et al. |
| 2005/0080356 A1 | 4/2005 | Dapolito et al. |
| 2005/0085847 A1 | 4/2005 | Galdonik et al. |
| 2005/0101987 A1 | 5/2005 | Salahieh |
| 2005/0131449 A1 | 6/2005 | Salahieh et al. |
| 2005/0137696 A1 | 6/2005 | Salahieh |
| 2005/0177132 A1 | 8/2005 | Lentz et al. |
| 2005/0209631 A1 | 9/2005 | Galdonik et al. |
| 2005/0277976 A1 | 12/2005 | Galdonik et al. |
| 2006/0015136 A1 | 1/2006 | Besselink |
| 2006/0015138 A1 | 1/2006 | Gertner |
| 2006/0030877 A1 | 2/2006 | Martinez et al. |
| 2006/0041188 A1 | 2/2006 | Dirusso et al. |
| 2006/0047301 A1 | 3/2006 | Ogle |
| 2006/0089618 A1 | 4/2006 | McFerran et al. |
| 2006/0089666 A1 | 4/2006 | Linder et al. |
| 2006/0100658 A1 | 5/2006 | Obana et al. |
| 2006/0100662 A1 | 5/2006 | Daniel et al. |
| 2006/0129180 A1 | 6/2006 | Tsugita et al. |
| 2006/0135961 A1 | 6/2006 | Rosenman et al. |
| 2006/0149350 A1 | 7/2006 | Patel et al. |
| 2006/0161241 A1 | 7/2006 | Barbut et al. |
| 2006/0200047 A1 | 9/2006 | Galdonik et al. |
| 2006/0200191 A1 | 9/2006 | Zadno-Azizi |
| 2006/0259066 A1 | 11/2006 | Euteneuer |
| 2007/0043259 A1 | 2/2007 | Jaffe et al. |
| 2007/0060944 A1 | 3/2007 | Boldenow et al. |
| 2007/0088244 A1 | 4/2007 | Miller et al. |
| 2007/0088383 A1 | 4/2007 | Pal et al. |
| 2007/0173878 A1 | 7/2007 | Heuser |
| 2007/0191880 A1 | 8/2007 | Cartier et al. |
| 2007/0208302 A1 | 9/2007 | Webster et al. |
| 2007/0244504 A1 | 10/2007 | Keegan et al. |
| 2008/0004687 A1 | 1/2008 | Barbut |
| 2008/0033467 A1 | 2/2008 | Miyamoto et al. |
| 2008/0058860 A1 | 3/2008 | Demond et al. |
| 2008/0065145 A1 | 3/2008 | Carpenter |
| 2008/0065147 A1 | 3/2008 | Mazzocchi et al. |
| 2008/0086110 A1 | 4/2008 | Galdonik et al. |
| 2008/0109088 A1 | 5/2008 | Galdonik et al. |
| 2008/0125848 A1 | 5/2008 | Kusleika et al. |
| 2008/0154153 A1 | 6/2008 | Heuser |
| 2008/0172066 A9 | 7/2008 | Galdonik et al. |
| 2008/0188884 A1 | 8/2008 | Gilson et al. |
| 2008/0234722 A1 | 9/2008 | Bonnette et al. |
| 2008/0262442 A1 | 10/2008 | Carlin et al. |
| 2008/0300462 A1 | 12/2008 | Intoccia et al. |
| 2009/0024072 A1 | 1/2009 | Criado et al. |
| 2009/0024153 A1 | 1/2009 | Don Michael |
| 2009/0069840 A1 | 3/2009 | Hallisey |
| 2009/0198269 A1 | 8/2009 | Hannes et al. |
| 2009/0203962 A1 | 8/2009 | Miller et al. |
| 2009/0254172 A1 | 10/2009 | Grewe et al. |
| 2009/0287187 A1 | 11/2009 | Legaspi et al. |
| 2009/0326575 A1 | 12/2009 | Galdonik |
| 2010/0004633 A1 | 1/2010 | Rothe et al. |
| 2010/0010476 A1 | 1/2010 | Galdonik et al. |
| 2010/0063537 A1 | 3/2010 | Ren et al. |
| 2010/0179583 A1 | 7/2010 | Carpenter et al. |
| 2010/0179584 A1 | 7/2010 | Carpenter et al. |
| 2010/0179585 A1 | 7/2010 | Carpenter et al. |
| 2010/0179647 A1 | 7/2010 | Carpenter et al. |
| 2010/0185216 A1 | 7/2010 | Garrison et al. |
| 2010/0211095 A1 | 8/2010 | Carpenter |
| 2010/0312268 A1 | 12/2010 | Belson |
| 2010/0324589 A1 | 12/2010 | Carpenter et al. |
| 2011/0066221 A1 | 3/2011 | White et al. |
| 2011/0282379 A1 | 11/2011 | Lee et al. |
| 2012/0046739 A1 | 2/2012 | von Oepen et al. |
| 2012/0095500 A1 | 4/2012 | Heuser |
| 2012/0172915 A1 | 7/2012 | Fifer et al. |
| 2012/0172916 A1* | 7/2012 | Fifer ................... A61F 2/013 606/200 |
| 2012/0172917 A1 | 7/2012 | Fifer et al. |
| 2012/0172919 A1 | 7/2012 | Fifer et al. |
| 2012/0203265 A1 | 8/2012 | Heuser |
| 2013/0131714 A1 | 5/2013 | Wang et al. |
| 2013/0231694 A1 | 9/2013 | Lashinski |
| 2014/0052170 A1 | 2/2014 | Heuser et al. |
| 2014/0094843 A1 | 4/2014 | Heuser |
| 2014/0100597 A1* | 4/2014 | Wang ................... A61F 2/01 606/200 |
| 2014/0243877 A9 | 8/2014 | Lee et al. |
| 2014/0282379 A1 | 9/2014 | Lee et al. |
| 2015/0039016 A1 | 2/2015 | Naor et al. |
| 2015/0209131 A1 | 7/2015 | Fifer et al. |
| 2015/0230910 A1 | 8/2015 | Lashinski et al. |
| 2015/0335416 A1 | 11/2015 | Fifer et al. |
| 2016/0058541 A1 | 3/2016 | Schotzko et al. |

FOREIGN PATENT DOCUMENTS

| | | |
|---|---|---|
| EP | 1253871 | 2/2007 |
| EP | 2303384 | 4/2011 |
| EP | 2391303 | 12/2011 |
| EP | 2480165 | 8/2012 |
| EP | 2658476 | 11/2013 |
| EP | 2387427 | 8/2014 |
| JP | 2003-505216 | 2/2003 |
| JP | 2003-526451 | 9/2003 |
| JP | 2003-290231 | 10/2003 |
| JP | 3535098 B2 | 6/2004 |
| JP | 2006-500187 | 1/2006 |
| JP | 2008-511401 | 4/2008 |
| JP | 2008-515463 | 5/2008 |
| JP | 2011-525405 | 9/2011 |
| WO | WO 99/23976 | 5/1999 |
| WO | WO 01/67989 | 9/2001 |
| WO | WO 2004/026175 | 4/2004 |
| WO | WO 2005/118050 | 12/2005 |
| WO | WO 2006/026371 | 3/2006 |
| WO | WO 2008/033845 | 3/2008 |
| WO | WO 2008/100790 | 8/2008 |
| WO | WO 2008/113857 | 9/2008 |
| WO | WO 2010/008451 | 1/2010 |
| WO | WO 2010/081025 | 7/2010 |
| WO | WO 2010/083527 | 7/2010 |
| WO | WO 2010/088520 | 8/2010 |
| WO | WO 2011/034718 | 3/2011 |
| WO | WO 2011/017103 | 10/2011 |
| WO | WO 2012/092377 | 7/2012 |

OTHER PUBLICATIONS

Final Office Action for U.S. Appl. No. 13/338,916 dated Jul. 5, 2013, in 13 pages.
Final Office Action for U.S. Appl. No. 13/338,957 dated Jul. 3, 2013, in 12 pages.
Final Office Action for U.S. Appl. No. 13/338,957 dated Apr. 23, 2014 in 13 pages.
Final Office Action for U.S. Appl. No. 13/338,966 dated Jun. 18, 2013, in 10 pages.
Final Office Action for U.S. Appl. No. 13/338,982 dated Jun. 26, 2013, in 11 pages.
Final Office Action for U.S. Appl. No. 13/338,995 dated Sep. 27, 2013, in 13 pages.
Final Office Action for U.S. Appl. No. 13/338,957 dated Jul. 21, 2015, in 7 pages.
Notice of Allowance for U.S. Appl. No. 13/338,916 dated Feb. 2, 2015, in 21 pages.
Notice of Allowance for U.S. Appl. No. 13/338,966 dated Jul. 9, 2014, in 21 pages.
Office Action for U.S. Appl. No. 13/338,914 dated Jan. 13, 2015, in 17 pages.
Office Action for U.S. Appl. No. 13/338,914 dated Dec. 15, 2015, in 9 pages.

(56) References Cited

OTHER PUBLICATIONS

Office Action for U.S. Appl. No. 13/338,916 dated Mar. 1, 2013, in 11 pages.
Office Action for U.S. Appl. No. 13/338,957 dated Jan. 2, 2015, in 8 pages.
Office Action for U.S. Appl. No. 13/338,957 dated Mar. 15, 2013, in 12 pages.
Office Action for U.S. Appl. No. 13/338,966 dated Mar. 14, 2013, in 9 pages.
Office Action for U.S. Appl. No. 13/338,982 dated Mar. 1, 2013, in 12 pages.
Office Action for U.S. Appl. No. 13/338,982 dated Oct. 24, 2014, in 7 pages.
Office Action for U.S. Appl. No. 13/338,995 dated Jun. 26, 2014, in 10 pages.
Office Action for U.S. Appl. No. 13/338,995 dated Mar. 1, 2013, in 11 pages.
Internet Archive Wayback Machine; Fiber Innovative Technology: FIT Capabilities; downloaded from http://web.archive.org/web/20010217040848/http://www.fitfibers.com/capabilities.htm (Archived Feb. 17, 2001; printed on Dec. 12, 2016).
Internet Archive Wayback Machine; Fiber Innovative Technology: 4DG Fibers; downloaded from http://web.archive.org/web/20011030070010/http://fitfibers.com/4DG_Fibers.htm (Archived Oct. 30, 2001; printed on Dec. 12, 2016).
Internet Archive Wayback Machine; Fiber Innovative Technology: FIT Products; downloaded from http://web.archive.org/web/20010408003529/http://www.fitfibers.com/product.htm (Archived Apr. 8, 2001; printed on Dec. 12, 2016).

\* cited by examiner

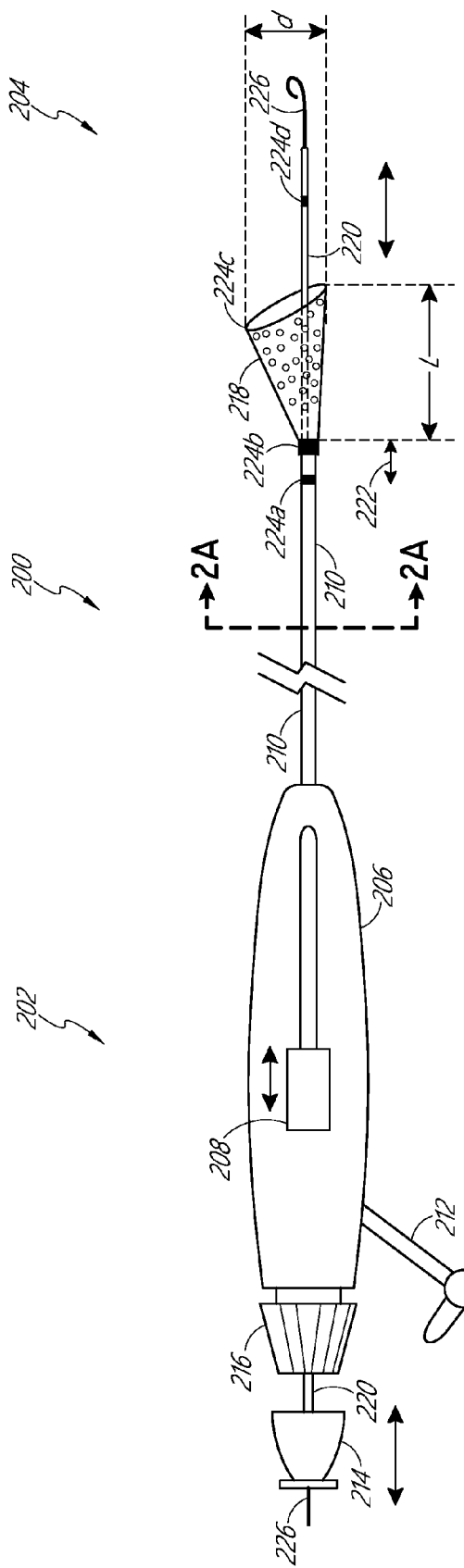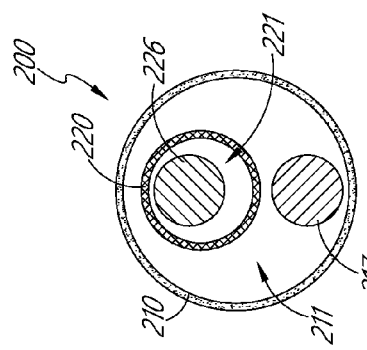

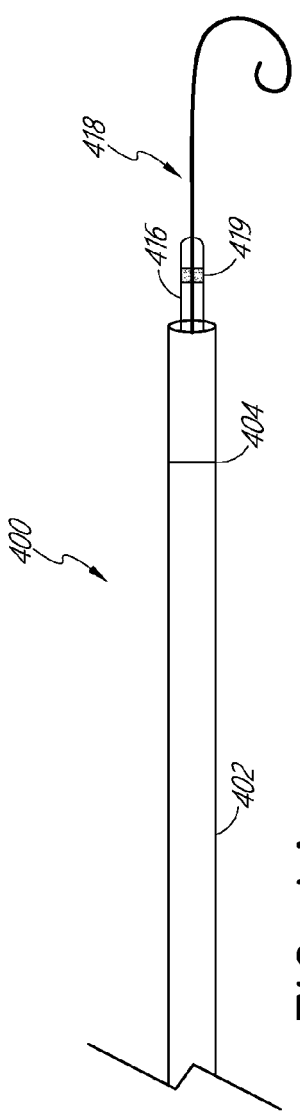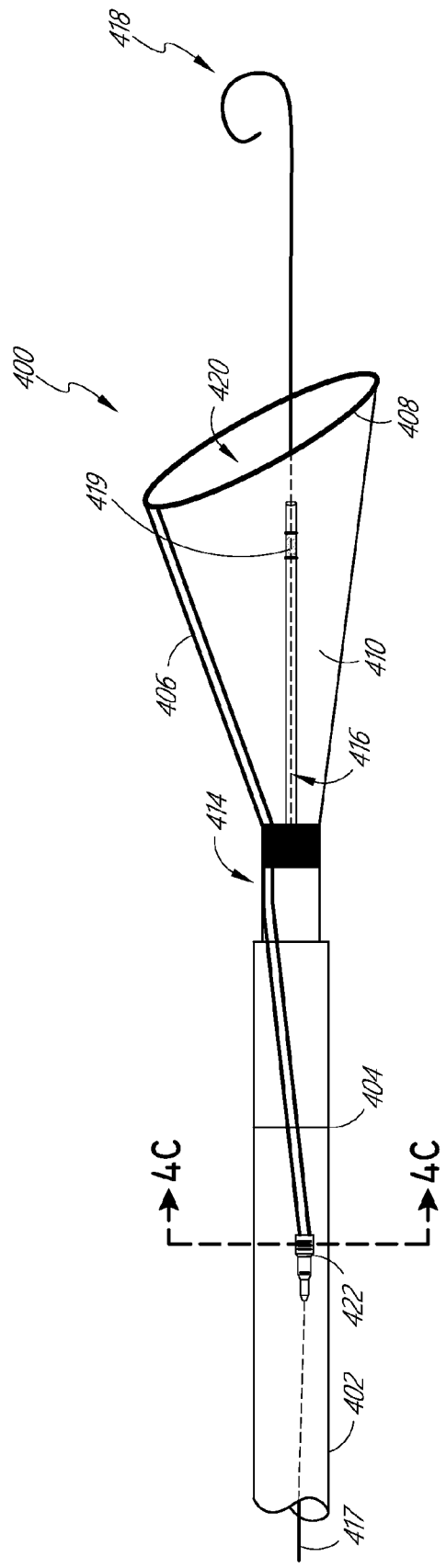
FIG. 4A
FIG. 4B

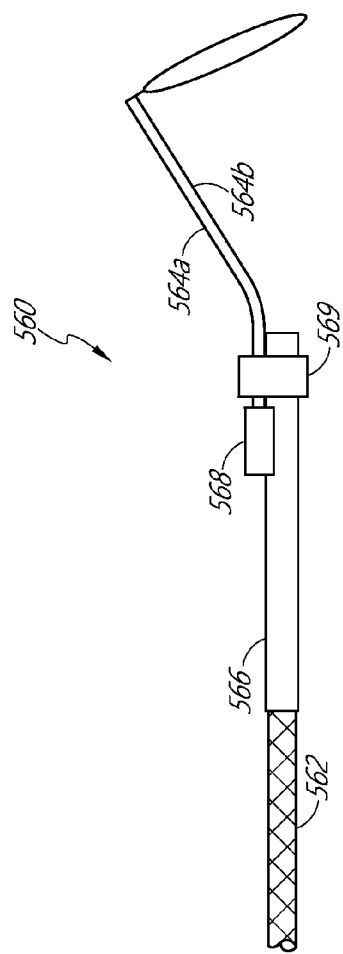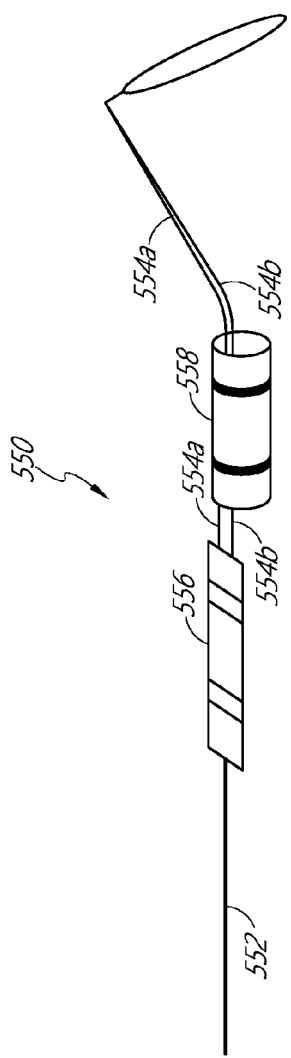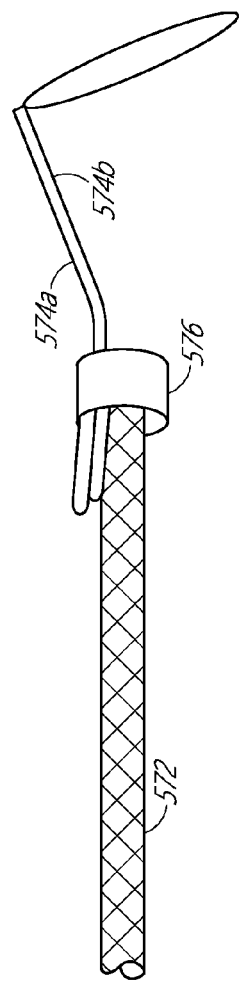

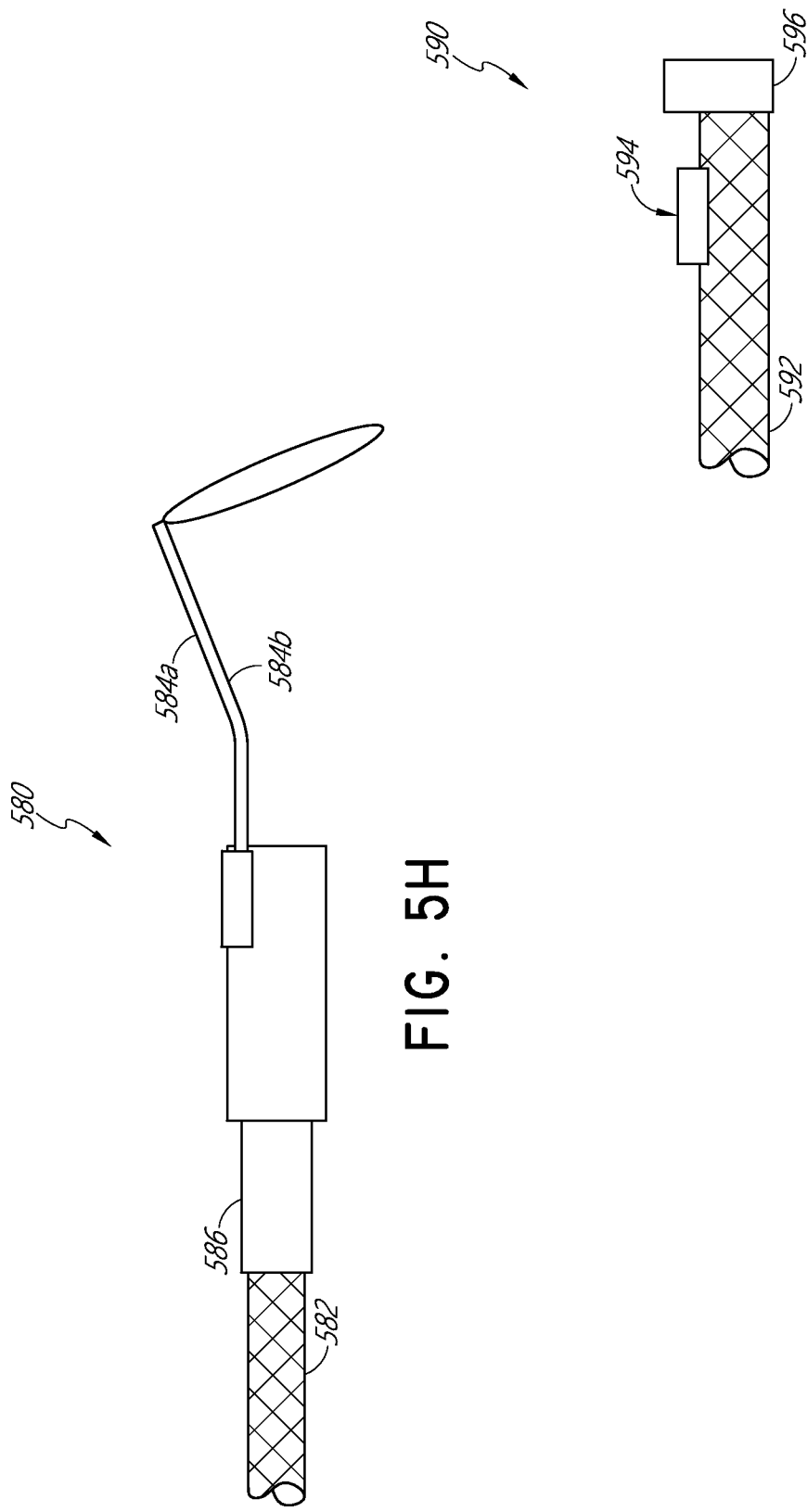

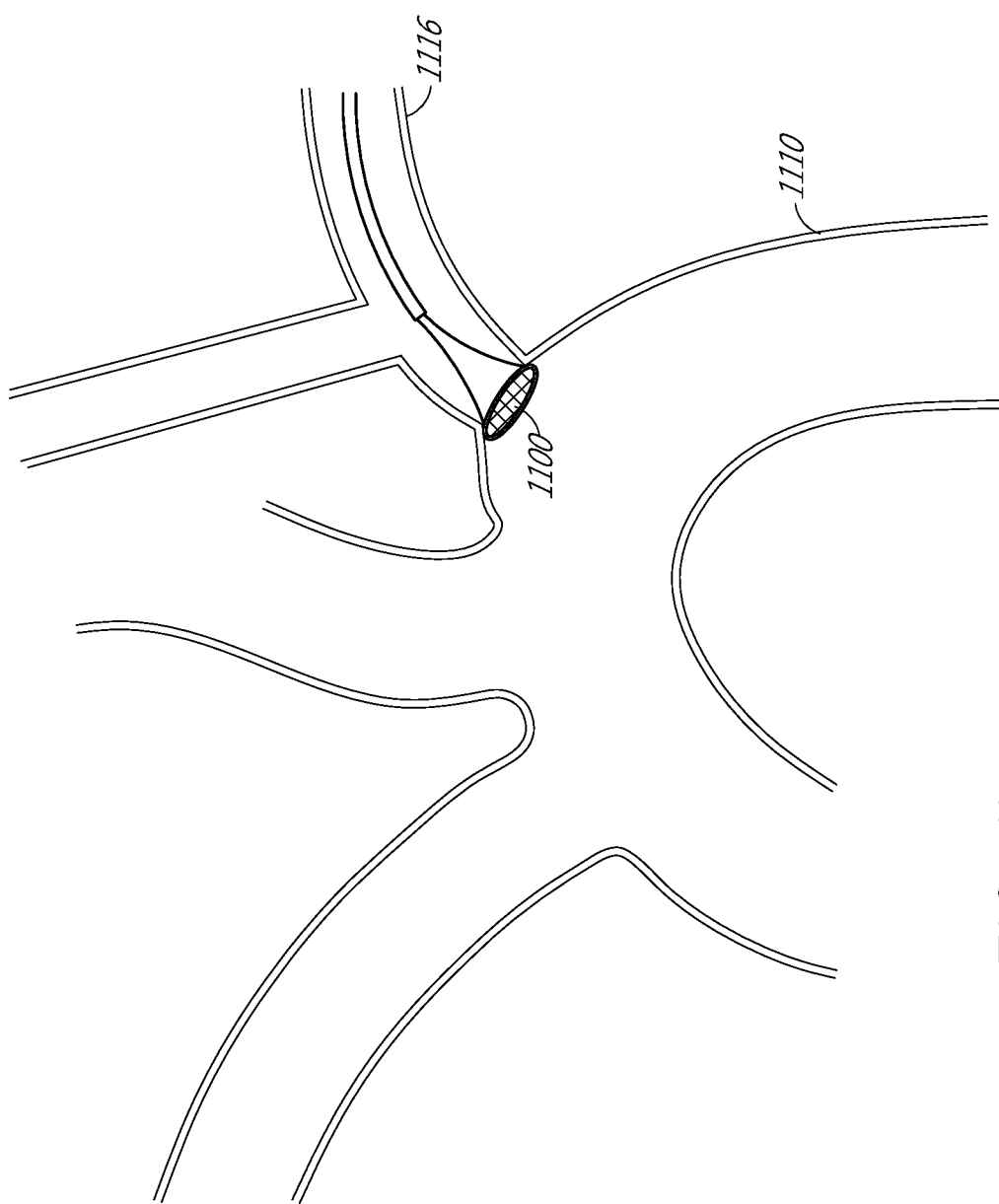

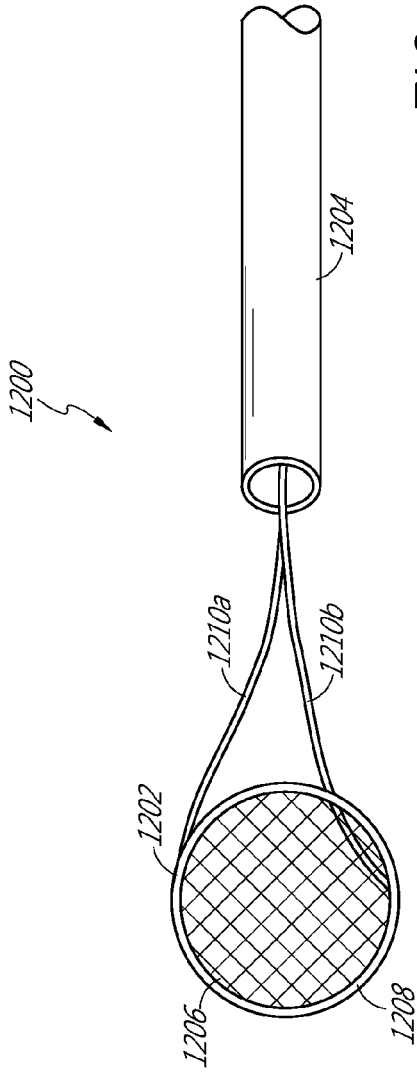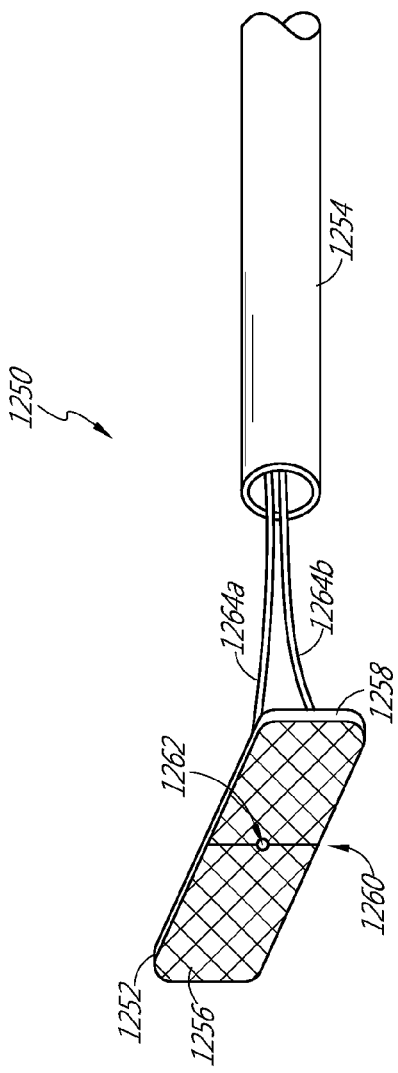

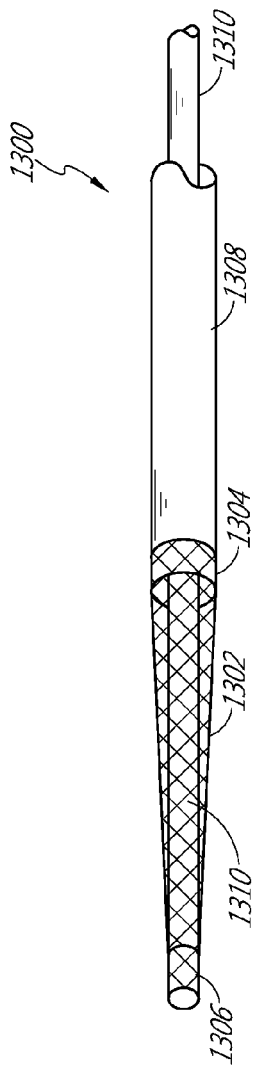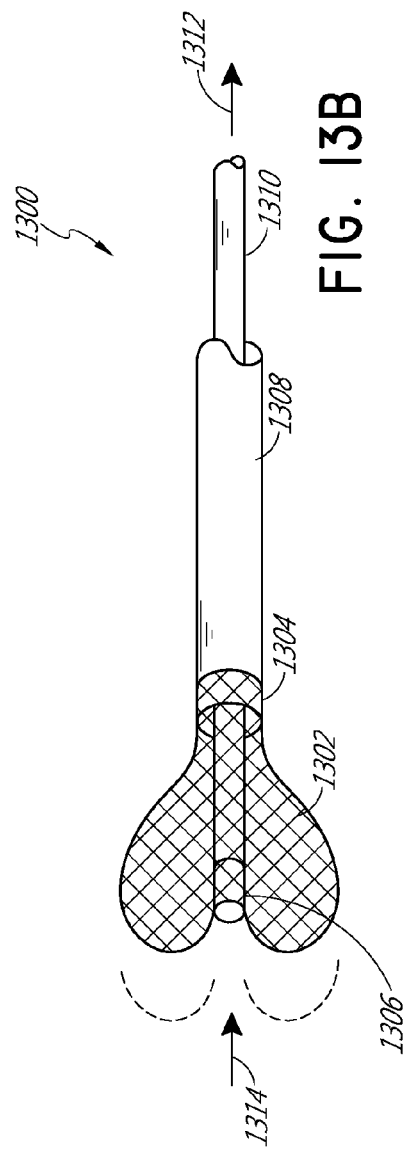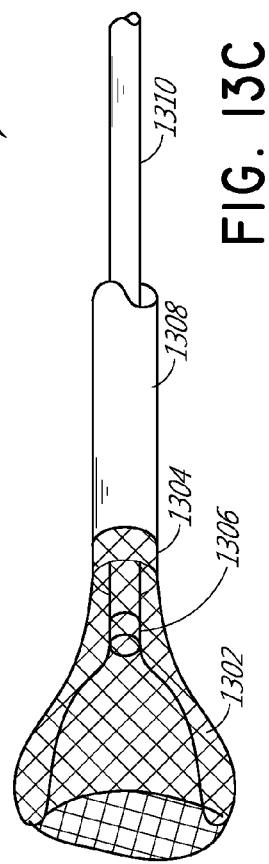

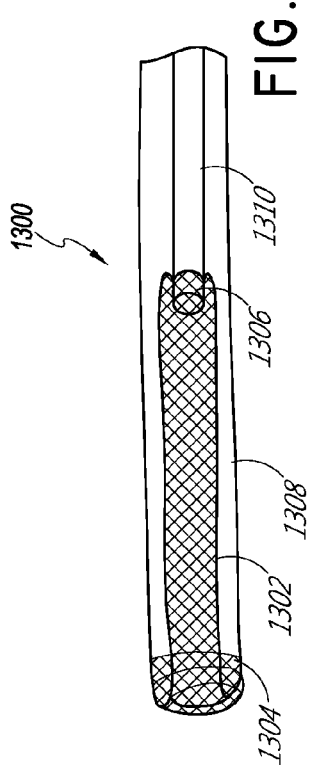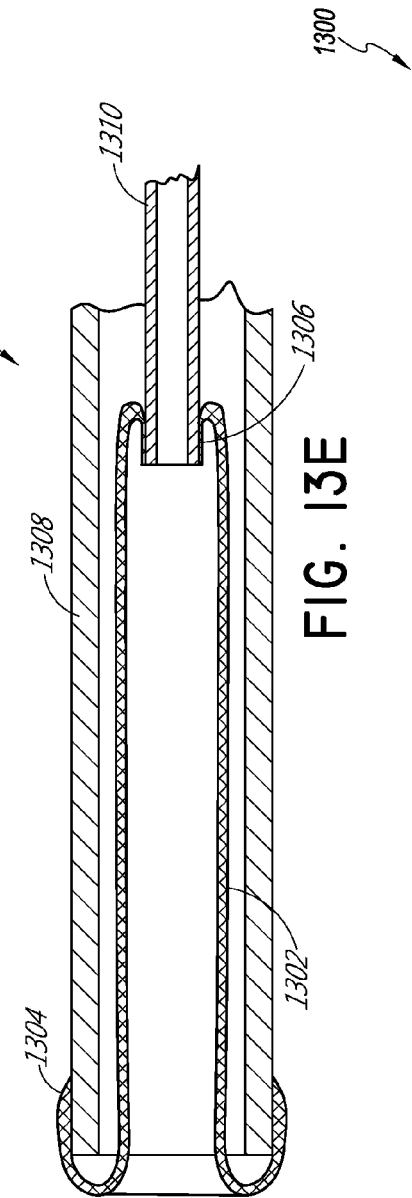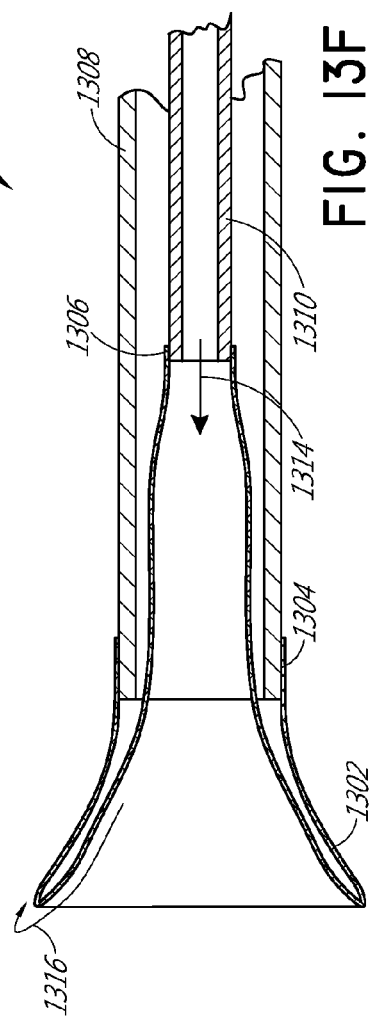

VASCULAR FILTERS, DEFLECTORS, AND METHODS

BACKGROUND

Field

The disclosure relates to devices and methods for filtering body fluids such as blood and/or selectively deflecting potentially embolic particles from the body fluid. The devices can be catheter-based for insertion into a vascular system of a subject.

Description of Related Art

Thromboembolic disorders, such as stroke, pulmonary embolism, peripheral thrombosis, atherosclerosis, and the like affect many people. These disorders are a major cause of morbidity and mortality in the United States and throughout the world. Thromboembolic events are characterized by an occlusion of a blood vessel. The occlusion can be caused by a clot which is viscoelastic (jelly-like) and comprises platelets, fibrinogen, and other clotting proteins.

Percutaneous aortic valve replacement procedures have become popular, but stroke rates related to this procedure are between four and twenty percent. During catheter delivery and valve implantation, plaque or other material may be dislodged from the vasculature and may travel through the carotid circulation and into the brain. When an artery is occluded by a clot or other embolic material, tissue ischemia (lack of oxygen and nutrients) develops. The ischemia progresses to tissue infarction (cell death) if the occlusion persists. Infarction does not develop or is greatly limited if the flow of blood is reestablished rapidly. Failure to reestablish blood-flow can lead to the loss of limb, angina pectoris, myocardial infarction, stroke, or even death.

Reestablishing blood flow and removal of the thrombus is highly desirable. Surgical techniques and medicaments to remove or dissolve obstructing material have been developed, but exposing a subject to surgery may be traumatic and is best avoided when possible. Additionally, the use of certain devices carry risks such as the risk of dislodging foreign bodies, damaging the interior lining of the vessel as the catheter is being manipulated, blood thinning, etc.

SUMMARY

Vascular filters and deflectors and methods for filtering bodily fluids are disclosed herein. A blood filtering assembly can capture embolic material dislodged or generated during an endovascular procedure to inhibit or prevent the material from entering the cerebral vasculature. A blood deflecting assembly can deflect embolic material dislodged or generated during an endovascular procedure to inhibit or prevent the material from entering the cerebral vasculature.

In some embodiments, a method of inhibiting embolic material from entering cerebral vasculature comprises positioning a guidewire in a left subclavian artery upstream of a left vertebral artery and tracking a distal portion of a protection device over the guidewire. The distal portion of the protection device comprises an outer sheath, an inner member radially inward of the outer sheath, and a self-expanding filter assembly radially between the outer sheath and the inner member. The inner member comprises a guidewire lumen. The method further comprises at least one of proximally retracting the outer sheath and distally advancing the self-expanding filter assembly to deploy the self-expanding filter assembly from the outer sheath in the left subclavian artery upstream of the left vertebral artery. The method may further comprise performing an endovascular procedure. The endovascular procedure may comprise mitral or atrial valve implantation or replacement. The deployed self-expanding filter assembly may inhibit embolic material from entering cerebral vasculature through the left vertebral artery during the endovascular procedure. The method may further comprise, after performing the endovascular procedure, withdrawing the self-expanding filter assembly from the left subclavian artery.

After deploying the self-expanding filter assembly, the inner member may prolapse into an aortic arch. The method may further comprise proximally retracting the inner member out of the aortic arch while the deployed self-expanding filter assembly remains in the left subclavian artery upstream of the left vertebral artery. The method may further comprise monitoring arterial pressure using the outer sheath. The method may further comprise providing fluid through the outer sheath. The method may further comprise positioning a filtering device in an innominate artery and a left common carotid artery. The filtering device may inhibit embolic material from entering cerebral vasculature through a right vertebral artery, a right common carotid artery, and the left common carotid artery during the endovascular procedure.

In some embodiments, a method of inhibiting embolic material from entering cerebral vasculature comprises positioning a distal portion of a protection device at a location. The location is in the left subclavian artery and/or the left vertebral artery. The distal portion of the protection device comprises an outer sheath and at least one of a self-expanding filter assembly and a self-expanding deflector assembly radially inward of the outer sheath. The method further comprises deploying the at least one of a self-expanding filter assembly and a self-expanding deflector assembly from the outer sheath at the location. The deployed self-expanding filter assembly and/or self-expanding deflector assembly inhibits embolic material from entering cerebral vasculature during an endovascular procedure.

The distal portion of the protection device may further comprise an inner member radially inward of the outer sheath. The inner member may comprise a guidewire lumen. Positioning the distal portion of the protection device at the location may comprise tracking the distal portion of the protection device over a guidewire. The method may further comprise monitoring arterial pressure using at least one of the inner member and the outer sheath. The distal portion of the protection device may comprise the self-expanding filter assembly. The distal portion of the protection device may comprise the self-expanding deflector assembly. The endovascular procedure may comprise atrial valve or mitral valve implantation or replacement. Deploying the at least one of a self-expanding filter assembly and a self-expanding deflector assembly may comprise proximally retracting the outer sheath. After deploying the at least one of a self-expanding filter assembly and a self-expanding deflector assembly, the inner member may prolapse into an aortic arch, and the method may further comprise proximally retracting the inner member out of the aortic arch while the deployed at least one of a self-expanding filter assembly and a self-expanding deflector assembly remains in the location. The method may further comprise positioning a filtering device in an innominate artery and a left common carotid artery. The filtering device may inhibit embolic material from entering cerebral vasculature through a right vertebral artery, a right common carotid artery, and the left common carotid artery during the endovascular procedure.

In some embodiments, an embolic material protection device configured to inhibit embolic material from entering cerebral vasculature through a left vertebral artery comprises an outer sheath, an inner member radially inward of the outer sheath, and a self-expanding filter assembly radially between the outer sheath and the inner member. The inner member comprises a lumen. The self-expanding filter assembly is deployable out of the outer sheath by at least one of proximally retracting the outer sheath and distally advancing the self-expanding filter assembly. The inner member may be longitudinally movable independent of the self-expanding filter assembly and the outer sheath.

The self-expanding filter assembly may have a diameter between 7 mm and 12 mm. The self-expanding filter assembly may have a diameter between 2 mm and 4.5 mm. The device may further comprise an arterial pressure monitoring device in fluid communication with the lumen of the outer sheath. A kit may comprising the device of and a filtering device configured to be positioned in an innominate artery and a left common carotid artery.

In some embodiments, an embolic material protection device configured to inhibit embolic material from entering cerebral vasculature through a left vertebral artery comprises an outer sheath and a deflector assembly. The deflector assembly may be deployable out of the outer sheath by at least one of proximally retracting the outer sheath and distally advancing the deflector assembly. The device may further comprise an inner member. The inner member may comprise a lumen. The deflector assembly may comprise a surface configured to be placed across an ostium of an artery. The deflector assembly may be coupled to a distal end of the outer sheath and a distal end of the inner member, and may comprise a frustoconical shape upon manipulation of at least one of the outer sheath and the inner member. The deflector assembly may comprise an at least partially arcuate surface configured to be placed across an ostium of the left vertebral artery.

BRIEF DESCRIPTION OF THE DRAWINGS

FIG. 2 illustrates an example protection device.
FIG. 2A is a cross-sectional view of the protection device of FIG. 2 taken along the line 2A-2A in FIG. 2.
FIG. 4A illustrates an example distal portion of a protection device in a delivery state.
FIG. 4B illustrates the example distal portion of FIG. 4A in a deployed state.
FIG. 5E illustrates an example coupling system.
FIG. 5F illustrates another example coupling system.
FIG. 5G illustrates yet another example coupling system.
FIG. 5H illustrates still another example coupling system.
FIG. 5I illustrates yet still another example coupling system.
FIG. 11 illustrates another example distal portion of a protection device in a deployed state in vasculature.
FIG. 12A illustrates an example protection device.
FIG. 12B illustrates another example protection device.
FIGS. 13A-13D illustrate another example protection device.
FIGS. 13E and 13F are cross-sectional views of the example protection device of FIGS. 13A-13D.

DETAILED DESCRIPTION

The disclosure generally relates to devices and methods for filtering fluids and/or deflecting debris contained within fluids, including body fluids such as blood. A filtering or deflecting device can be positioned in an artery before and/or during an endovascular procedure (e.g., transcatheter aortic valve implantation (TAVI) or replacement (TAVR), transcatheter mitral valve implantation (TAMI) or replacement (TAMR), surgical aortic valve replacement (SAVR), other surgical valve repair, implantation, or replacement, cardiac ablation (e.g., ablation of the pulmonary vein to treat atrial fibrillation) using a variety of energy modalities (e.g., radio frequency (RF), energy, cryo, microwave, ultrasound), cardiac bypass surgery (e.g., open-heart, percutaneous), transthoracic graft placement around the aortic arch, valvuloplasty, etc.) to inhibit or prevent embolic material such as debris, emboli, thrombi, etc. resulting from entering the cerebral vasculature.

The devices may be used to trap particles in other blood vessels within a subject, and they can also be used outside of the vasculature. The devices described herein are generally adapted to be delivered percutaneously to a target location within a subject, but can be delivered in any suitable way and need not be limited to minimally-invasive procedures.

Figure 1:
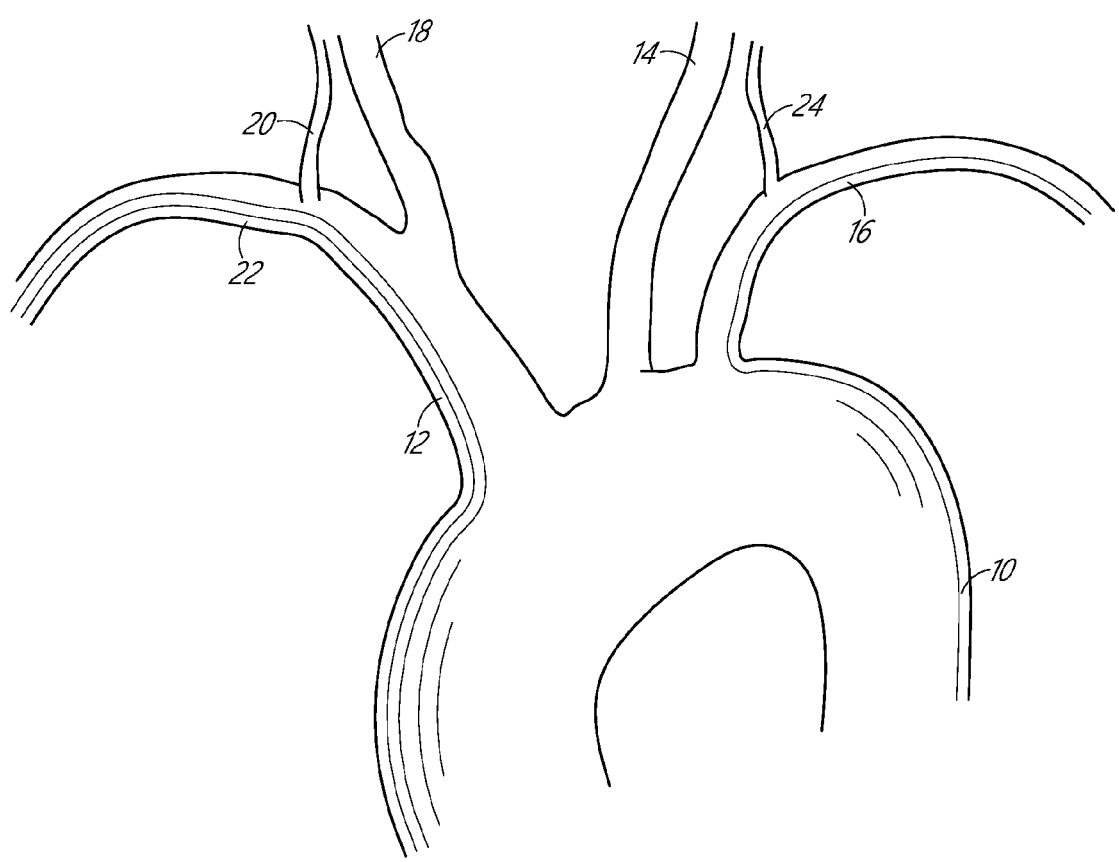
FIG. 1 is a schematic perspective view of an aortic arch.

FIG. 1 is a schematic perspective view of an aortic arch 10. The aortic arch 10 is upstream of the left and right coronary arteries. The aortic arch 10 typically includes three great branch arteries: the brachiocephalic artery or innominate artery 12, the left common carotid artery 14, and the left subclavian artery 16. The innominate artery 12 branches to the right carotid artery 18, then the right vertebral artery 20, and thereafter is the right subclavian artery 22. The right subclavian artery 22 supplies blood to, and may be directly accessed from (termed right radial access), the right arm. The left subclavian artery 16 branches to the left vertebral artery 24, usually in the shoulder area. The left subclavian artery 16 supplies blood to, and may be directly accessed from (termed left radial access), the left arm. Four of the arteries illustrated in FIG. 1 supply blood to the cerebral vasculature: (1) the left carotid artery 14 (about 40% of cerebral blood supply); (2) the right carotid artery 18 (about 40% of cerebral blood supply); (3) the right vertebral artery 20 (about 10% of cerebral blood supply); and (4) the left vertebral artery 24 (about 10% of cerebral blood supply). The devices and methods described herein are also compatible with the prevalent (27%) bovine variant.

Devices and methods, some of which are compatible and/or synergistic with the devices and methods described herein, have been developed to filter blood flowing to the innominate artery 12 and the left common carotid artery 14, which provide about 90% of the blood entering the cerebral vasculature. Examples are provided in U.S. Pat. No. 8,876, 796, which is incorporated herein by reference in its entirety, and most particularly with respect to disclosure directed to devices and methods for protecting aortic arch branch arteries and structures of filter devices. Certain such devices and methods leave the left subclavian artery 16, and thus the left vertebral artery 24, which provides about 10% of the blood entering the cerebral vasculature, exposed to potential embolic material. Other embodiments described in U.S. Pat. No. 8,876,796 filter blood flowing to the left common carotid artery 14 and the left subclavian artery 16. Certain such devices and methods leave the innominate artery 12, and thus both the right common carotid artery 18 and the right vertebral artery 20, which provide even about 50% of the blood entering the cerebral vasculature, exposed to potential embolic material. Assuming perfect use and operation, either of these options may leave potential stroke rates as high as two to ten percent due to exposed arteries that provide blood flow to the cerebral vasculature.

FIG. 2 illustrates an example protection device 200. The protection device 200 can inhibit or prevent embolic material from entering the cerebral vasculature by protecting a cerebral artery (e.g., the left vertebral artery) during an endovascular procedure. Protection of the left vertebral artery using the protection device 200 can reduce the risk of stroke in procedures with no other embolic protection by about 10%. Protection of the left vertebral artery using the protection device 200 (e.g., in the left subclavian artery or the left vertebral artery) can reduce the risk of stroke in procedures with another embolic protection such as described in U.S. Pat. No. 8,876,796 positioned in the innominate artery and the left common carotid artery to less than about 5%, less than about 3%, less than about 1%, or almost nil. Protection of the innominate artery using the protection device 200 can reduce the risk of stroke in procedures with no other embolic protection by about 50%. Protection of the innominate artery using the protection device 200 can reduce the risk of stroke in procedures with another embolic protection such as described in U.S. Pat. No. 8,876,796 positioned in the left common carotid artery and the left subclavian artery to less than about 5%, less than about 3%, less than about 1%, or almost nil.

The protection device 200 comprises a proximal portion 202 and a distal portion 204. The proximal portion 202 is configured to be held and manipulated by a user such as a surgeon. The distal portion 204 is configured to be positioned at a target location such as the left subclavian artery or the left vertebral artery. The location is preferably proximate to the ostium of the artery. When the distal portion 204 is configured to be positioned at the left subclavian artery, the location is preferably upstream of the left vertebral artery.

The proximal portion 202 comprises a handle 206, a control 208 such as a slider, an outer sheath 210, a port 212, optionally an inner member translation control 214 such as a knob, and optionally a hemostasis valve control 216 such as a knob. Although not visible in FIG. 2, the proximal portion 202 also comprises an inner member 220 radially inward of the outer sheath 210. Although not visible in FIG. 2, the proximal portion 202 also comprises a filter wire 217 (FIG. 2A) radially inward of the outer sheath 210. The filter wire 217 is coupled to the filter assembly 218 in the distal portion 204. The outer sheath 210 may have a diameter between about 4 French (Fr) (approximately 1.33 millimeters (mm)) and about 6 Fr (approximately 2 mm) (e.g., about 5 Fr (approximately 1.67 mm)). The outer sheath 210 may comprise an atraumatic distal tip. Other features of the protection device 200 and other protection devices described herein may be flexible and/or atraumatic. The outer sheath 210 may comprise a curvature, for example based on an intended placement location (e.g., the left subclavian artery and/or the left vertebral artery).

The slider 208 can be used to translate the outer sheath 210 and/or a filter assembly 218 (e.g., coupled to a filter wire). For example, the slider 208 may proximally retract the outer sheath 210, the slider 208 may distally advance the filter assembly 218 out of the outer sheath 210, or the slider 208 may proximally retract the outer sheath 210 and distally advance the filter assembly 218 (e.g., simultaneously or serially), which can allow the filter assembly 218 to radially expand. The slider 208 may also be configured to have an opposite translation effect, which can allow the filter assembly 218 to be radially collapsed (e.g., due to compression by the outer sheath 210) as the filter assembly 218 is drawn into the outer sheath 210. Other deployment systems are also possible, for example comprising gears or other features such as helical tracks (e.g., configured to compensate for any differential lengthening due to foreshortening of the filter assembly 218, configured to convert rotational motion into longitudinal motion), a mechanical element, a pneumatic element, a hydraulic element, etc. for opening and/or closing the filter assembly 218.

The port 212 is in fluid communication with the inner member 220 (e.g., via a Y-shaped connector in the handle 206). The port 212 can be used to flush the device (e.g., with saline) before, during, and/or after use, for example to remove air. The port 212 can also or alternatively be used to monitor blood pressure at the target location, for example by connecting an arterial pressure monitoring device in fluid communication with a lumen 221 (FIG. 2A) of the outer sheath 210. The port 212 can be also or alternatively be used to inject contrast agent, dye, thrombolytic agents such as tissue plasminogen activator (t-PA), etc. The slider 208 preferably does not interact with the inner member 220 such that the inner member 220 is longitudinally movable independent of the filter assembly 218 and the outer sheath 210. The inner member translation control 214 can be used to longitudinally translate the inner member 220, for example before, after, and/or during deployment of the filter assembly 218. The inner member translation control 214 may comprise a slider in the housing 206 (e.g., separate from the slider 208).

The rotatable hemostasis valve control 216 can be used to reduce or minimize fluid loss through the protection device 200 during use. For example, when positioned in the left subclavian artery, the direction of blood flow with respect to the device 200 will be distal to proximal, so blood may be otherwise inclined to follow the pressure drop out of the device 200. The hemostasis valve control 216 is illustrated as being rotatable, but other arrangements are also possible (e.g., longitudinally displaceable). The hemostasis valve control 216 may be configured to fix relative positions of the outer sheath 210 and the filter assembly 218, for example as described with respect to the hemostasis valve in U.S. Pat. No. 8,876,796. The hemostasis valve 216 may comprise, for example, an elastomeric seal and HV nut.

The distal portion 204 comprises the outer sheath 210, a filter assembly 218 radially inward of the outer sheath 210, and optionally the inner member 220. The filter assembly 218 may be radially between the outer sheath 210 and the inner member 220 (e.g., radially inward of the outer sheath 210 and the inner member 220 radially inward of the filter assembly 218) in a delivery state or shape or position.

The filter assembly 218 may comprise a self-expanding filter assembly (e.g., comprising a superelastic material with stress-induced martensite due to confinement in the outer sheath 210). The filter assembly 218 may comprise a shape-memory material configured to self-expand upon a temperature change (e.g., heating to body temperature). The filter assembly 218 may comprise a shape-memory or superelastic frame (e.g., comprising a distal end hoop comprising nitinol) and a microporous material (e.g., comprising a polymer including laser-drilled holes) coupled to the frame, for example similar to the filter assemblies described in U.S. Pat. No. 8,876,796.

The filter assembly 218 may be coupled (e.g., crimped, welded, soldered, etc.) to a distal end of a deployment wire or filter wire 217. The filter wire 217 can comprise a rectangular ribbon, a round (e.g., circular, elliptical) filament, a portion of a hypotube, a braided structure (e.g., as described herein), combinations thereof, and the like. The filter wire 217 can be coupled to the handle 206 and/or the slider 208 to provide differential longitudinal movement versus the outer sheath 210, as shown by the arrows 222, which can sheathe and unsheathe the filter assembly 218 from the outer sheath 210.

FIG. 2A is a cross-sectional view of the protection device 200 of FIG. 2 taken along the line 2A-2A in FIG. 2. The inner member 220 is in the lumen 211 of the outer sheath 210. The inner member 220 may be coaxial with the outer sheath 210. The guidewire 226 is in the lumen 221 of the inner member 220. The guide wire 226 may be coaxial with the inner member 220. The filter wire 217 is also in the outer sheath 210, for example to one side of the inner member 220. In implementations in which the filter wire 217 comprises a deployment tube (e.g., as described herein), the deployment tube may be coaxial with and radially between the outer sheath 210 and the inner member 220.

The filter assembly 218 in an expanded, unconstrained state has a maximum diameter or effective diameter (e.g., if the mouth is in the shape of an ellipse) d. The diameter d can be between about 1 mm and about 15 mm (e.g., at least about 1 mm, about 2 mm, about 3 mm, about 4 mm, about 5 mm, about 6 mm, about 7 mm, about 8 mm, about 9 mm, about 10 mm, about 11 mm, about 12 mm, about 13 mm, about 14 mm, about 15 mm, ranges between such values, etc.). In some embodiments (e.g., when the filter assembly is configured to be positioned in the left subclavian artery), the diameter d is between about 7 mm and about 12 mm (e.g., about 7 mm, about 8 mm, about 9 mm, about 10 mm, about 11 mm, about 12 mm, ranges between such values, etc.). In some embodiments (e.g., when the filter assembly is configured to be positioned in the left vertebral artery), the diameter d is between about 2 mm and about 4.5 mm (e.g., about 2 mm, about 2.5 mm, about 3 mm, about 3.5 mm, about 4 mm, about 4.5 mm, ranges between such values, etc.). Other diameters d or other types of lateral dimensions are also possible. Different diameters d can allow treatment of a selection of subjects having different vessel sizes.

The filter assembly 218 has a maximum length l. The length l can be between about 7 mm and about 50 mm (e.g., at least about 7 mm, about 8 mm, about 9 mm, about 10 mm, about 11 mm, about 12 mm, about 13 mm, about 14 mm, about 15 mm, about 16 mm, about 17 mm, about 18 mm, about 19 mm, about 20 mm, about 21 mm, about 22 mm, about 23 mm, about 24 mm, about 25 mm, about 30 mm, about 35 mm, about 40 mm, about 45 mm, about 50 mm, ranges between such values, etc.). Other lengths l are also possible, for example based on the diameter or effective diameter d. For example, the length l of the filter assembly 218 may increase as the diameter d increases, and the length l of the filter assembly 218 may decrease as the diameter d decreases. A distance from an apex of the mouth of the filter assembly 218 to an elbow in the frame may be about 35 mm. Different lengths l can allow treatment of a selection of subjects having different vessel sizes.

The inner member 220 is optional, but can provide additional uses and/or advantages in combination with the filter assembly 218. For example, the inner member 220 may comprise a guidewire lumen 221, allowing the device 200 to be tracked over a guidewire (e.g., the guidewire 226 comprising a pigtail distal end) without contacting the filter assembly 218. For another example, a lumen 221 of the inner member 220 may be fluidly coupled to the flush port 212, which can allow flushing of fluid through the inner member 220, for example to remove air. For yet another example, a lumen 221 of the inner member 220 may be connected to an arterial pressure monitoring device, allowing measurement of pressure proximate to the location of the filter assembly 218.

The distal portion 204 may include fluoroscopic markers 224a, 224b, 224c, 224d to aid a user in positioning the device 200, deploying the filter assembly 218, utilizing the inner member 220, etc. The fluoroscopic marker 224a is proximate to a distal end of the outer sheath 210. The fluoroscopic marker 224b is proximate to a proximal end of the filter assembly 218. The fluoroscopic marker 224c is proximate to a proximal end of a ring of the filter assembly 218. The fluoroscopic marker 224d is proximate to a distal end of the inner member 220. The fluoroscopic markers may comprise a radiopaque material (e.g., iridium, platinum, tantalum, gold, palladium, tungsten, tin, silver, titanium, nickel, zirconium, rhenium, bismuth, molybdenum, combinations thereof, and the like). More or fewer fluoroscopic markers are also possible.

The protection device 200 is illustrated as comprising a guidewire 226 therethrough, although the guidewire 226 may be characterized as being separate from the protection device 200, for example independently sold, packaged, and/or directed. The guidewire 226 may extend through a lumen of the outer sheath 210. The lumen may be configured to receive a guidewire 226 having a diameter between about 0.014 inches and about 0.025 inches. The guidewire 226 may extend through a lumen of the filter assembly 218. The guidewire 226 may extend through a lumen 221 of the inner member 220. For example, the protection device 200 may be tracked over the guidewire 226 to position the protection device 200 at a desired location.

Figure 3:
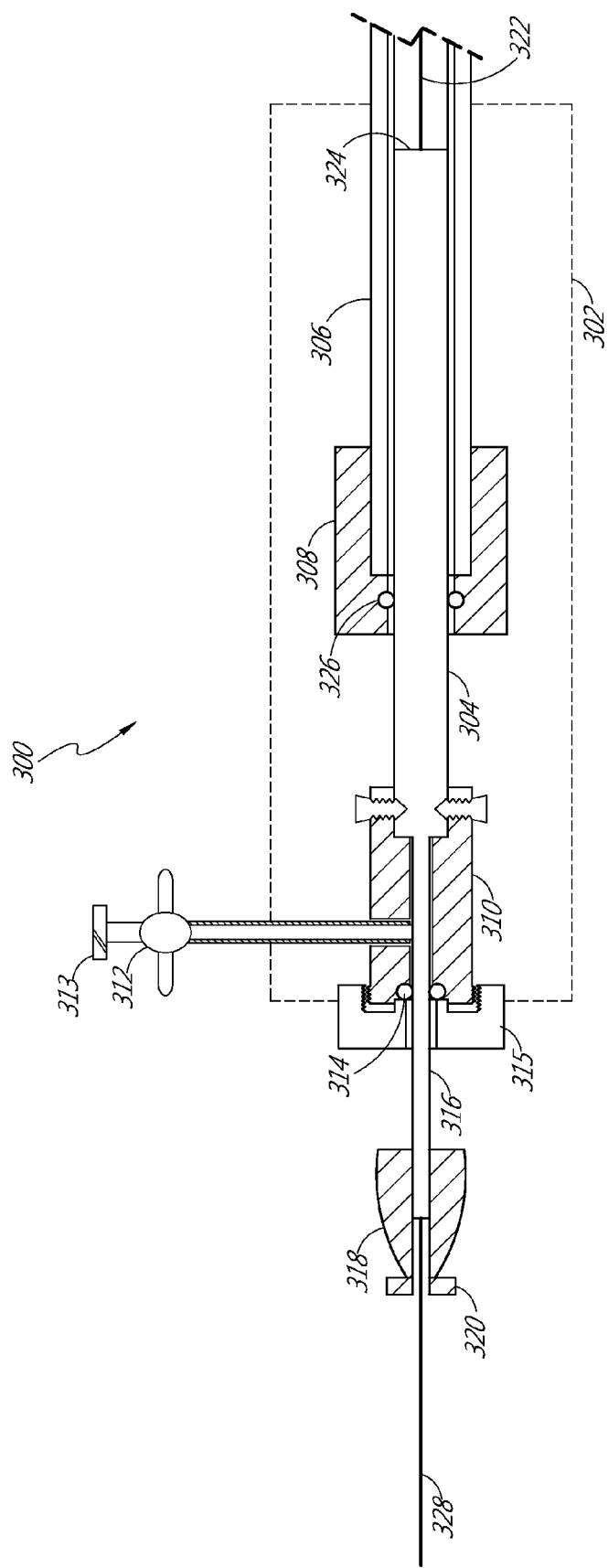
FIG. 3 is a side cross-sectional view of an example proximal portion of a protection device.

FIG. 3 is a side cross-sectional view of an example proximal portion 300 of a protection device (e.g., the protection device 200). The proximal portion 300 comprises a housing or shell 302 (e.g., the handle 206), a deployment tube 304, an outer sheath 306 (e.g., the outer sheath 210) around the deployment tube 304, a slider 308 (e.g., the slider 208), a deployment hub 310, a stopcock 312, a hemostatis valve/cap 314, an inner member 316 (e.g., the inner member 220), an inner member hub slider 318, and a luer fitting 320. One or more of the illustrated features may optionally be omitted from the proximal portion 300, for example to reduce cost, to reduce complexity, to remove features not used, etc. The addition of features not illustrated in FIG. 3 is also possible.

The housing 302 can hold parts of the proximal portion 300 together, protect parts from contaminants (e.g., that may interfere with use of the proximal portion 300), and the like. The housing 302 may be omitted, for example providing a user of the proximal portion 300 unfettered access or control over every feature of the proximal portion 300. For example, many users are quite skilled at manipulating wires and tubes with respect to each other such that a slider 308 or the like may reduce manipulation dexterity. For other users, a slider 306 or the like may provide aid in proper use, for example providing a fail-safe limited range of movement.

A filter wire 322 that is coupled to a filter assembly (e.g., as described herein) may be coupled to the deployment tube 304 by a weld 324 or other coupling means. The housing 302 allows the slider 308 to move longitudinally, for example in a track in the housing 302, to deploy a filter assembly (e.g., out of a distal end of the outer sheath 306). The deployment housing 304 can help maintain positions of elements such as the filter wire 322 and the outer sheath 306 during movement such as translation of the slider 308. The proximal portion 300 may comprise a static seal 326 between the slider 308 and the deployment tube 304. The housing 302 can provide ergonomic interaction between a user and the proximal portion 300.

The luer fitting 320 allows the proximal portion 300 to be flushed (e.g., with saline) prior to use (e.g., through the lumen of the inner member 316), for example to remove air. The luer fitting 320 may be used to couple the inner member 316 to a pressure monitoring device. The proximal portion 300 is illustrated with a guidewire 328 extending through a lumen of the inner member 316, indicative that the lumen of the inner member 316 may be used to guide a protection device to a location by tracking over the guidewire 328. The stopcock 312 includes a luer fitting port 313 in fluid communication with the outer sheath lumen 221 and is suitable for use in monitoring arterial blood pressure. If the inner member 316 is too small for an accurate measurement or if the inner member 316 is omitted, the outer sheath 304 can provide the fluid lumen used to measure blood pressure.

A lock 315 may be provided to releasably engage the inner member 316 to inhibit or prevent the inner member 316 from moving with respect to the hub 310. Other interaction mechanisms are also possible.

Figure 4C:
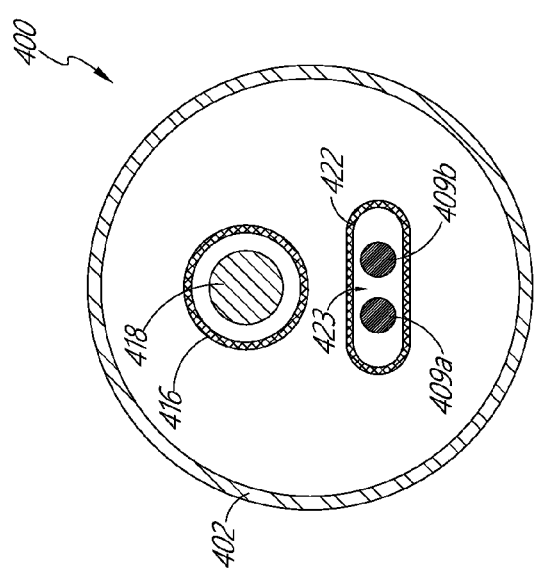
FIG. 4C is a cross-sectional view of the distal portion of FIGS. 4A and 4B along the line 4C-4C of FIG. 4B.

FIG. 4A illustrates an example distal portion 400 of a protection device (e.g., the protection device 200) in a collapsed or delivery state or shape with the filter retracted within the outer sheath 402. FIG. 4B illustrates the example distal portion 400 of FIG. 4A in an expanded or deployed state or shape with the outer sheath 402 retracted to expose the filter assembly 406. The distal portion 400 comprises an outer sheath 402 (e.g., the outer sheath 210), a radiopaque marker or band 404 (e.g., the radiopaque marker 224a), a filter assembly 406 (e.g., the filter assembly 218), an inner member 416 (e.g., the inner member 220), a radiopaque marker or band 419 (e.g., the radiopaque marker 224d), and a guide tube 414. One or more of the illustrated features may optionally be omitted from the distal portion 400, for example to reduce cost, to reduce complexity, to remove features not used, etc. The addition of features not illustrated in FIGS. 4A-4D is also possible.

The radiopaque marker 404 may be proximate to the distal end of the outer sheath 402 to help guide the distal end of the outer sheath 402 into a delivery location (e.g., the left subclavian artery upstream of the left vertebral artery, or the left vertebral artery). The radiopaque marker 404 may be positioned to aid a user in determining a deployed position of the filter assembly 406, for example accounting for foreshortening upon radial expansion. Once the radiopaque marker 404 is aligned with a target location or some distance proximal or distal to the target location, the filter assembly 406 can be deployed, or the distal portion 400 may be advanced or retracted a certain distance before the filter assembly 406 is deployed. The radiopaque marker 404 may be omitted (e.g., by using a radiopaque portion of the filter assembly 406). The radiopaque marker 404 may be used to determine a degree of deployment of the filter assembly 406. For example, if the proximal end of the filter assembly 406 comprises a radiopaque marker or band such as the radiopaque marker or band 224b in FIG. 2, full deployment of the filter assembly 406 may be indicated by the radiopaque marker 224b being aligned with the radiopaque marker 404 and/or distal to the radiopaque marker 404. The radiopaque marker 404 may be used to determine a degree of retraction of the inner member 416. For example, retraction of the distal end of the inner member 416 into the outer sheath 401 may be indicated by the radiopaque marker 419 being aligned with the radiopaque marker 404 and/or proximal to the radiopaque marker 404.

In the delivery state illustrated in FIG. 4A, the filter assembly 406 is within outer sheath 402. In the delivery state, the distal portion 400 is radially compact, which can facilitate navigation through vasculature (e.g., through vasculature of the arm). As described herein, the outer sheath 402 and the filter assembly 406 are longitudinally movable relative to each other. When a position of the filter assembly 406 is distal to a position of the outer sheath 402 (e.g., due to proximal retraction of the outer sheath 402 and/or distal advancement of the filter assembly 406 via the filter wire 417 via the guide tube 414), the filter assembly 406 exits the distal end of the outer sheath 402 and self-expands to the deployed state illustrated in FIG. 4B. The inner member 416 may be movable independent of the outer sheath 402 and the filter assembly 406. In the deployed state, the filter assembly 406 can inhibit embolic material from entering cerebral vasculature (e.g., by filtering blood flowing to the left vertebral artery).

The filter assembly 406 comprises a support element or frame 408 and a filter element 410. The frame 408 generally provides expansion support to the filter element 410 in the expanded state. In the expanded state, the filter element 410 is configured to filter fluid (e.g., blood) flowing through the filter element 410 and to inhibit or prevent particles (e.g., embolic material) from flowing through the filter element 410 by capturing the particles in the filter element 410.

Figure 4D:
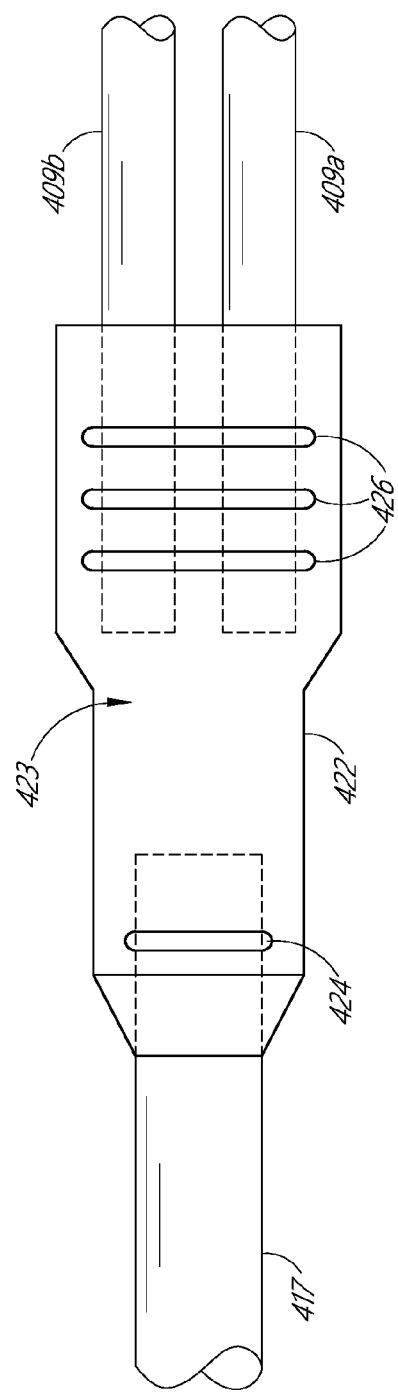
FIG. 4D is an enlarged view of part of the distal portion of FIGS. 4A and 4B.

The guide tube 414 and/or the outer sheath 402 may comprise a lumen in which portions of the frame 408 (e.g., longitudinal portions) are coupled (e.g., adhesively joined, banded, crimped, welded, soldered, etc.) to a filter wire 417. The coupled portions of the frame 408 and filter wire 417 may be in a lumen 423 of a crimp tube 422 that is in the guide tube 414. FIG. 4C is a cross-sectional view of the distal portion 400 of FIGS. 4A and 4B along the line 4C-4C of FIG. 4B. FIG. 4C shows the guidewire 418 in the inner member 416, which is in the outer sheath 402. A crimp tube 422 is also in the outer sheath 402. The filter wire 417 and wires 409a, 409b of the frame 408 of the filter assembly 406 are coupled in the crimp tube 422. FIG. 4D is an enlarged view of part of the distal portion 400 of FIGS. 4A and 4B. A proximal portion of the crimp tube 422 is coupled to the filter wire 417 by a crimp 424 and a distal portion of the crimp tube 422 is coupled to the wires 409a, 409b of the frame 408 of the filter assembly 406 by a plurality of longitudinally offset crimps 426. Other coupling mechanisms as described herein are also possible. The guide tube 414 may provide a platform for placement of radiopaque bands. The inner member 416 may extend through the lumen of the guide tube 414.

The inner member 416 may extend the length of the filter assembly 406 in the compressed state, for example to inhibit or prevent the guidewire 418 from interacting with the filter assembly 406, thereby inhibiting or preventing the filter assembly 406 from binding the guidewire 418 during navigation. Foreshortening of the filter assembly 406 during deployment may result in the inner member 420 extending distally to the filter assembly 408 after deployment of the filter assembly 406, possibly into the aortic arch. The inner member 420 may be proximally retracted (e.g., out of the aortic arch and/or for other reasons such as positioning for use of a therapeutic, radiopaque, or other fluid, for use with a pressure monitor, etc.) after deployment of the filter assembly 406, for example as described with respect to FIG. 6B. The inner member 420 may be distally advanced before retraction of the filter assembly 406, for example to inhibit or prevent the guidewire 418 from interacting with the filter assembly 406, thereby inhibiting or preventing the filter assembly 406 from binding the guidewire 418 during navigation.

The frame 408 is configured to engage or appose the inner walls of a lumen (e.g., blood vessel) in which the distal portion 400 is expanded. The frame 408 may comprise or be constructed of, for example, nickel titanium (e.g., nitinol), nickel titanium niobium, chromium cobalt (e.g., MP35N, 35NLT), copper aluminum nickel, iron manganese silicon, silver cadmium, gold cadmium, copper tin, copper zinc, copper zinc silicon, copper zinc aluminum, copper zinc tin, iron platinum, manganese copper, platinum alloys, cobalt nickel aluminum, cobalt nickel gallium, nickel iron gallium, titanium palladium, nickel manganese gallium, stainless steel, combinations thereof, and the like. The frame 408 may comprise a wire (e.g., having a round (e.g., circular, elliptical) or polygonal (e.g., square, rectangular) cross-section). For example, in some embodiments, the frame 408 comprises a straight piece of nitinol wire shape set into a circular or oblong hoop or hoop with one or two straight legs running longitudinally along or at an angle to a longitudinal axis of the distal portion 400. At least one of the straight legs may be coupled to a filter wire 417, for example as shown in FIG. 4C. The straight legs may be on a long side of the filter assembly 406 (e.g., the bottom side as illustrated in FIG. 4B) and/or on a short side of the filter assembly 406 (e.g., the top side as illustrated in FIG. 4B). The frame 408 forms a shape of an opening 420 of the filter assembly 406. The opening 420 may be circular, elliptical, or any shape that can appropriately appose sidewalls of a vessel such as the left subclavian artery or the left vertebral artery. As shown in FIG. 4B, the filter assembly 406, for example for implementations intended for use in the left subclavian artery, has a generally distally-facing opening 420.

The frame 408 may include a radiopaque marker such as a small coil wrapped around or coupled to the hoop to aid in visualization under fluoroscopy. In some embodiments, the frame may not comprise a shape other than a hoop, for example a spiral. In some embodiments, the filter assembly 406 may not include or be substantially free of a frame.

In some embodiments, the frame 408 and the filter element 410 form an oblique truncated cone having a non-uniform or unequal length around and along the length of the filter assembly 406. In such a configuration, along the lines of a windsock, the filter assembly 406 has a larger opening 420 (upstream) diameter and a reduced ending (downstream) diameter (e.g., proximate to the filter wire).

The filter element 410 comprises pores configured to allow blood to flow through the filter element 410, but that are small enough to inhibit prevent particles such as embolic material from passing through the filter element 410. The filter element 410 may comprise a filter membrane such as a polymer (e.g., polyurethane, polytetrafluoroethylene (PTFE)) film mounted to the frame 406. The filter element may have a thickness between about 0.0001 inches and about 0.03 inches (e.g., no more than about 0.0001 inches, about 0.001 inches, about 0.005 inches, about 0.01 inches, about 0.015 inches, about 0.02 inches, about 0.025 inches, about 0.03 inches, ranges between such values, etc.).

The film may comprise a plurality of pores or holes or apertures extending through the film. The film may be formed by weaving or braiding filaments or membranes and the pores may be spaces between the filaments or membranes. The filaments or membranes may comprise the same material or may include other materials (e.g., polymers, non-polymer materials such as metal, alloys such as nitinol, stainless steel, etc.). The pores of the filter element 410 are configured to allow fluid (e.g., blood) to pass through the filter element 410 and to resist the passage of embolic material that is carried by the fluid. The pores can be circular, elliptical, square, triangular, or other geometric shapes. Certain shapes such as an equilateral triangular, squares, and slots may provide geometric advantage, for example restricting a part larger than an inscribed circle but providing an area for fluid flow nearly twice as large, making the shape more efficient in filtration verses fluid volume. The pores may be laser drilled into or through the filter element 410, although other methods are also possible (e.g., piercing with microneedles, loose braiding or weaving). The pores may have a lateral dimension (e.g., diameter) between about 10 micron (μm) and about 1 mm (e.g., no more than about 10 μm, about 50 μm, about 100 μm, about 150 μm, about 200 μm, about 250 μm, about 300 μm, about 400 μm, about 500 μm, about 750 μm, about 1 mm, ranges between such values, etc.). Other pore sizes are also possible, for example depending on the desired minimum size of material to be captured.

The material of the filter element 410 may comprise a smooth and/or textured surface that is folded or contracted into the delivery state by tension or compression into a lumen. A reinforcement fabric may be added to or embedded in the filter element 410 to accommodate stresses placed on the filter element 410 during compression. A reinforcement fabric may reduce the stretching that may occur during deployment and/or retraction of the filter assembly 406. The embedded fabric may promote a folding of the filter to facilitate capture of embolic debris and enable recapture of an elastomeric membrane. The reinforcement material could comprise, for example, a polymer and/or metal weave to add localized strength. The reinforcement material could be imbedded into the filter element 410 to reduce thickness. For example, imbedded reinforcement material could comprise a polyester weave mounted to a portion of the filter element 410 near the longitudinal elements of the frame 408 where tensile forces act upon the frame 408 and filter element 410 during deployment and retraction of the filter assembly 406 from the outer sheath 402.

A fluid (e.g., blood) flows through the opening 420 and passes through the pores in the filter element 410, while the filter element 410 traps particles (e.g., embolic material) to inhibit or prevent passage to a location downstream of the filter assembly 406 such as the cerebral vasculature.

The distal portion 400 is illustrated with a guidewire 418 extending through a lumen of the inner member 416, indicative that the lumen of the inner member 416 may be used to guide a protection device to a location by tracking over the guidewire 418.

FIGS. 5A-5I illustrate optional variations on the protection devices described above. One or more of the variations may be applied, or all may be omitted. One or more of the variations may be applied to other protection devices described herein.

Figure 5B:
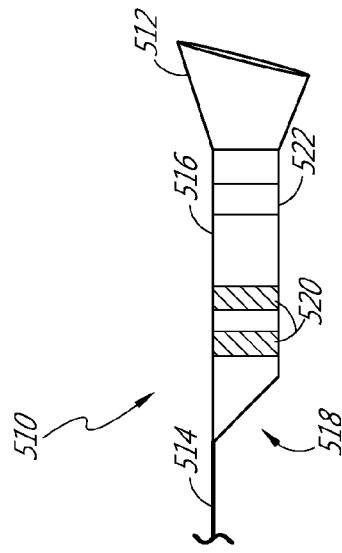
FIG. 5B illustrates an example coupling system.
Figure 5D:
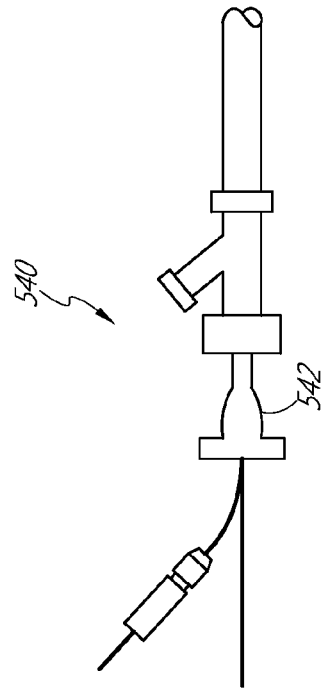
FIG. 5D illustrates an example inner member manipulation tool.
Figure 5A:
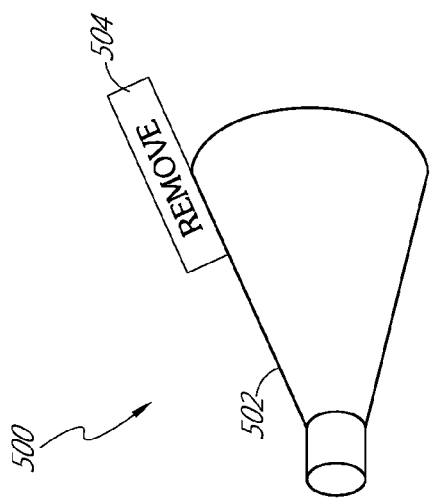
FIG. 5A illustrates an example guidewire loading tool.

FIG. 5A illustrates an example guidewire loading tool 500. A kit may comprise a protection device as described herein and the guidewire loading tool 500. The guidewire loading tool has a funnel shape 502 configured to facilitate placement of a proximal end of a guidewire into the protection device (e.g., into the lumen of the inner member of a protection device). The narrow portion of the funnel shape 502 may be sized to fit in a distal end of an inner member. The narrow portion of the funnel shape 502 may be sized to fit around a distal end of an inner member. In certain such implementations, the funnel shape 502 may comprise a step configured to interact with the distal end of the inner member to reduce or eliminate a step due to a blunt distal end of an inner member. The guidewire loading tool 500 may include indicia 504 to caution that the guidewire loading tool 500 is temporary and should be removed prior to tracking the protection device over the guidewire. A protection device may be packaged with the guidewire loading tool 500 in place (e.g., engaged with an inner member), for example to reduce or eliminate the user from engaging the guidewire loading tool 500 with a protection device. The guidewire loading tool or packaging insert 500 can protect the filter frame from being damaged in shipping and handling and protects the filter film during loading of the inner member and/or guidewire during initial assembly.

FIG. 5B illustrates an example coupling system 510. The coupling system 510 may couple a filter assembly 512 to a filter wire 514, for example by way of a guide tube 516. Referring again to the guide tube 414 illustrated in FIG. 4B, the proximal end of the guide tube 414 may be distal to the distal end of the outer sheath 402 when the filter assembly 406 is deployed. If the filter assembly 406 is retracted back into the outer sheath 402, the proximal end of the guide tube 414 may catch or snag on the distal end of the outer sheath 402, inhibiting or preventing retraction and/or dislodging embolic material captured by the filter assembly 406. The guide tube 516 of the coupling system 510 comprises a chamfered proximal end 518 configured to inhibit or prevent the proximal end 518 from catching or snagging on the distal end of an outer sheath. The chamfered proximal end may aid in routing the filter wire 514 through the protection device and/or coupling to the filter assembly 512. The coupling system 510 optionally comprises radiopaque marker bands 520, 522 that may aid a user in placement of the filter assembly 512 at a location. The use of a pair of bands for the radiopaque marker 520 may differentiate distal from proximal. The filter wire 514 may be coupled to wires of the frame of the filter assembly 512 by a crimp tube (e.g., a crimp tube 422 as described with respect to FIGS. 4B-4D) in the guide tube 516 or proximal to the guide tube 516. The angled proximal end 514 can facilitate loading of proximal bond into an outer sheath during initial assembly since, if the filter assembly 512 is extended beyond the outer sheath, a square or perpendicular cut may get caught on the distal end of the outer sheath.

Figure 5C:
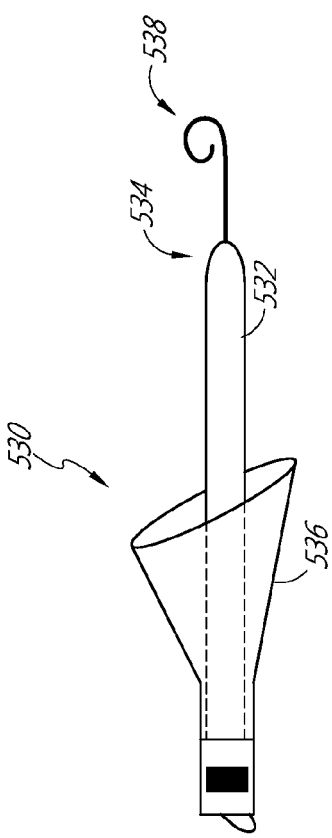
FIG. 5C illustrates another example coupling system.

FIG. 5C illustrates another example coupling system 530. The inner member 532 extends distal to the filter assembly 536. The inner member 532 comprises an atraumatic tapered distal tip 534. The atraumatic tapered distal tip 534 can provide easier advancement of the inner member 532 through vasculature (e.g., if the inner member 532 is distal to the distal end of an outer sheath such as illustrated in FIG. 4A). The atraumatic tapered distal tip 534 can provide easier advancement of the inner member 532 through the filter assembly 536 (e.g., a bond region of a filter wire and frame wires), for example after the inner member 532 has been retracted for pressure sensing, to be out of the aortic arch, etc. The atraumatic tapered distal tip 534 can provide easier interaction with a tapered proximal end of a guide tube (e.g., the proximal end 518 of the guide tube 516 shown in FIG. 5B). The atraumatic tapered distal tip 534 can provide easier tracking of the protection device over the guidewire 538 and through the vasculature.

FIG. 5D illustrates an example inner member manipulation tool 540. Tubing of the inner member may be floated through an area where a filter assembly is coupled to a filter wire and routed to a handle. The inner member may be coupled to a luer fitting 542, which can be manipulated to distally advance and/or longitudinally retract the inner member. A Y-connector includes a male luer fitting and a hemostasis valve on a top of the Y and a female luer connection on a bottom of the Y. The female luer connection can be connected to a guide catheter or outer sheath. The male luer fitting can be used for connection to a blood pressure sensing device. A filter deployment wire and inner member can be routed through the hemostasis valve of the male luer fitting to create a seal. The luer fitting 542 may provide an interface for a syringe (e.g., to flush the protection device and/or the vessel, to provide contrast agent, etc.), a pressure monitor, etc.

FIG. 5E illustrates an example coupling system 550. A filter wire 552 is coupled to wires 554a, 554b of a filter assembly frame by crimping and/or laser welding within a barrel 556 that is proximal to a guide tube 558. One wire, two wires (e.g., as shown in FIG. 5E), or more are possible depending on the structure of the frame of the filter assembly. The coupling may be sized to keep the filter assembly concentric in an outer sheath. The coupling may be sized (e.g., undersized) to allow for blood pressure monitoring with a guidewire in place (e.g., through the guide tube 558). The barrel 556 may comprise a chamfered proximal end configured to inhibit or prevent the proximal end from catching or snagging on the distal end of an outer sheath.

FIG. 5F illustrates another example coupling system 560. The filter wire is replaced with a deployment tube 562, for example comprising a woven or braided shaft, a laser cut or heat treated hypotube, combinations thereof, and the like. A barrel 566 is coupled to the deployment tube 562 by crimping, adhesive joining, and/or laser welding the barrel 566 around the deployment tube 562. The barrel 566 may comprise a thin wall, which can provide flexibility of the barrel 566. Wires 564a, 564b of a filter assembly frame are coupled to the barrel 566, for example by crimping and/or welding at site 568, which couples the filter assembly frame to the deployment tube 562 via the barrel 566. The coupling system 560 may comprise a radiopaque marker 569, for example comprising a platinum iridium ring. The radiopaque marker or band 569 may be used to mechanically join the filter frame wires 564a, 564b to the guide tube 5558. The radiopaque marker 569 may be coupled (e.g., crimped and/or welded) to a distal end of the barrel 566. The wires 564a, 564b may be radially between the barrel 566 and the radiopaque marker 569, for example to provide further coupling of the wires 564a, 564b to the barrel 566. A guidewire may be inserted through a lumen of the deployment tube 562. An inner member may be in a lumen of the deployment tube 562 or outside a lumen of the deployment tube 562. Blood pressure may be taken outside of the deployment tube 562.

FIG. 5G illustrates yet another example coupling system 570. As described with respect to the coupling system 560 of FIG. 5F and as applicable to other coupling systems described herein, the filter wire is replaced with a deployment tube 572. The deployment tube 572 may comprise polymer (e.g., polyimide) filaments. Wires 574a, 574b of a filter assembly frame are each four-way crimped to the deployment tube 572. The coupling system 570 may comprise a radiopaque marker 576, for example comprising a platinum iridium ring. Absent a guide tube, barrel, etc. that might include radiopaque markers and/or act as a stop mechanism, the radiopaque marker 576 can indicate the position of the filter assembly. The radiopaque marker 576 may be coupled (e.g., crimped, adhesively joined, and/or welded) to a distal end of the deployment tube 572. The wires 574a, 574b may be radially between the deployment tube 572 and the radiopaque marker 576, for example to provide further coupling of the wires 574a, 574b to the deployment tube 572. The coupling system 570 may provide a lower profile. The coupling system 570 may be devoid of a stiff transition between the filter assembly frame and the deployment tube 572. An inner member may be in a lumen of the deployment tube 572 or outside a lumen of the deployment tube 572.

Blood pressure may be taken inside of the deployment tube 572. For example, if an outer sheath around the deployment tube 572 is 5 Fr (approximately 1.67 mm), then measurement of blood pressure inside the deployment tube 572 may allow for true 5 Fr. Blood pressure may be taken outside of the deployment tube 572, although an outer sheath around the deployment tube 572 is preferably 6 Fr (approximately 2 mm) to obtain appropriate pressure measurements. Other diameters may also be appropriate (e.g., 5 Fr (approximately 1.67 mm) in an outer sheath or catheter or for a needle-based system.

In some embodiments in which a protection device comprises the coupling mechanism 570, a smaller guidewire may be used, for example to fit within a lumen of the deployment tube 572, which may be reduced where the deployment tube 572 is coupled to the wires 574a, 574b. A guidewire may be guided through the deployment tube 572 using a porous centering part, which can comprise a braid-reinforced shaft. The coupling may rely on an interference fit between the wires 574a, 574b and the braided shaft 572 when the band 576 is positioned over the wires 574a, 574b and the braided shaft 572. The band 576 may be mechanically swaged to hold the wires 574a, 574b in place. The filter assembly may be fixed to an inner member around which the deployment tube 572 is positioned, and the guidewire may be routed through a lumen of the inner member.

FIG. 5H illustrates still another example coupling system 580. The coupling system 580 comprises a deployment tube 582 and a strain relief heat shrink 586 around the distal end of the deployment tube 582. Wires 584a, 584b of a filter assembly frame may be coupled to the deployment tube 582, the strain relief heat shrink 586, a guide tube (e.g., as shown in FIG. 5H), other couplings described herein, and the like.

FIG. 5I illustrates yet still another example coupling system 590. The coupling system 590 comprises deployment tube 592 comprising a recess 594 in which a portion of a barrel such as a laser-cut tubing may be coupled (e.g., crimped). The recess 594 may be formed, for example by laser ablation of the deployment tube 592. The recess 594 and barrel portion may create mechanical interference, for example for coupling the deployment tube 592 to wires of a filter assembly frame. The coupling system 590 may comprise a radiopaque band 596 coupled to a distal end of the deployment tube 592.

Figure 6A:
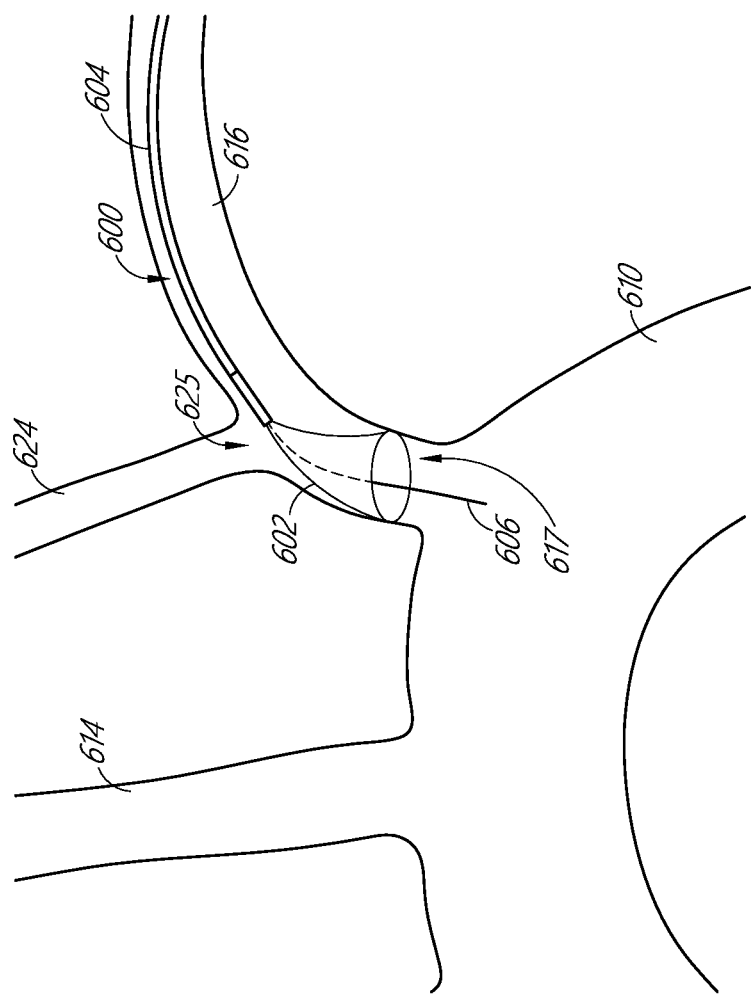
FIGS. 6A and 6B illustrate method of using an example distal portion of a protection device in a deployed state in target vasculature.
Figure 6B:
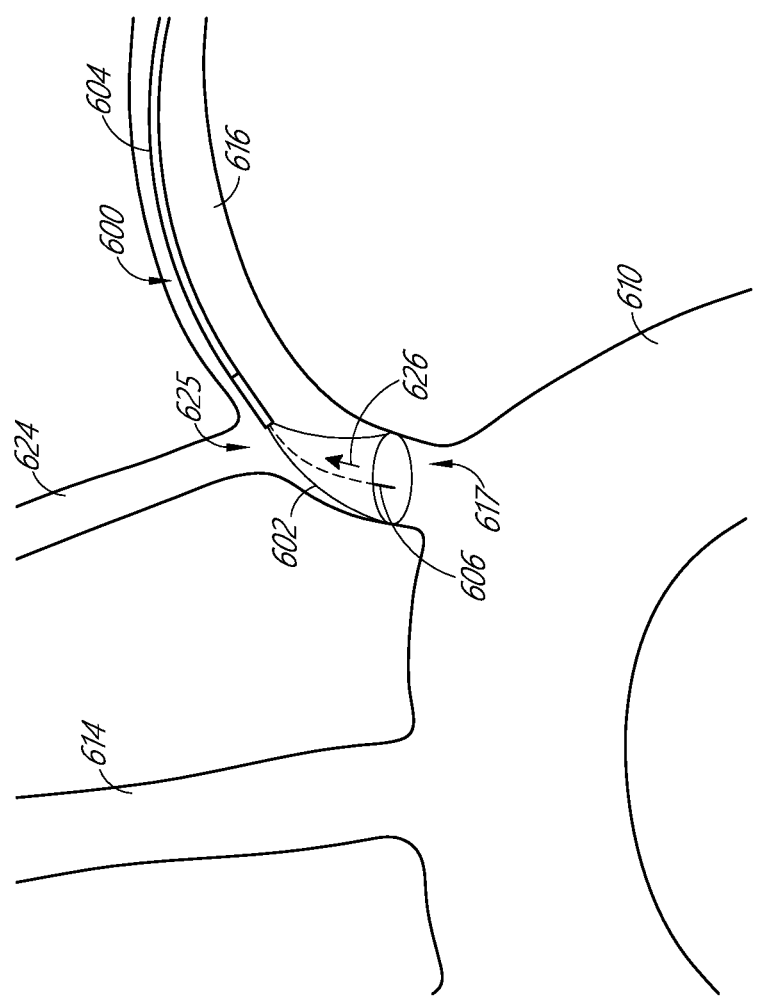

FIGS. 6A and 6B illustrate method of using an example distal portion of a protection device 600 in a deployed state in vasculature. A user would like to protect cerebral vasculature (e.g., the left vertebral artery 624) from embolic debris during an endovascular procedure such as TAVI. The user has decided to place the filter assembly 602 in the left subclavian artery 616 upstream of the left vertebral artery 624. The user may choose a protection device 600 comprising a distal-facing filter assembly 602 having a diameter between about 7 mm and about 12 mm. The protection device 600 may be packaged in a sterile coiled packaging. The protection device 600 may comprise an outer sheath 604 having a diameter of about 5 Fr (approximately 1.67 mm). The outer sheath 604 may include a curvature, for example complementing the size and orientation of the filter assembly 602. The outer sheath 604 may be steerable (e.g., a pullwire-controlled sheath).

Lumens of the protection device 600, for example a lumen of the outer sheath 604 and a lumen of the inner member 606, may be flushed (e.g., using saline) once or several times before, during, and/or after the procedure. The filter assembly 602 of the protection device 600 may be flushed and/or submerged (e.g., in a bowl of saline). Flushing and/or submerging of the filter assembly 602 may be with the filter assembly 602 in the outer sheath 604 (e.g., in the compressed state) and/or with the filter assembly 602 out of the outer sheath 604 (e.g., in the deployed state). If the filter assembly 602 is flushed and/or submerged in the deployed state, the filter assembly 602 may be compressed into the outer sheath 604 before use.

An artery in the left arm is accessed, for example using a 5 Fr introducer. A guidewire (e.g., having a diameter between about 0.014 inches and about 0.25 inches) is steered, traversing retrograde to blood flow, into or towards the left subclavian artery 616. A proximal end of the guidewire may be inserted into a distal end of the protection device 600, for example into a distal end of an inner member 606. The protection device 600 may be tracked over the guidewire until the distal end of the protection device 600 extends beyond a distal end of the introducer. In some implementations, the guidewire and the protection device 600 may be tracked together, with the guidewire leading the device 600 (e.g., advance the guidewire a distance, then advance the device 600 over the guidewire approximately the same distance). The guidewire and the inner member 606 may both be floppy or lack rigidity, they may be introduced inside the outer sheath 604 and then advanced ahead of the device 600 in the vasculature. The guidewire may be advanced at least about 6 centimeters (cm) distal to the distal end of the protection device 600.

The protection device 600 may be tracked or distally advanced over the guidewire until the distal end of the protection device 600 is at a desired location such as proximate to the left subclavian artery ostium 617, just above the aortic arch 610. Tracking of the protection device 600 may be under fluoroscopy, for example using radiopaque markers (e.g., at a distal end of the outer sheath 604 and/or the inner member 606) and/or radiopaque fluid or contrast media. Radiopaque fluid may be provided through the inner member 606 or outer sheath 604. The protection device 600 is preferably positioned so that the filter assembly 602 is upstream of the left vertebral artery 624 or more preferably proximate to the ostium 617 so that the filter assembly 602 can inhibit or prevent embolic material from entering the cerebral vasculature through the left vertebral artery 624. Using terminology of the procedure rather than blood flow, the protection device 600 is preferably positioned so that the filter assembly 602 is distal to the point in the left subclavian artery 616 where the left vertebral artery 624 branches off. Positioning may be based on available anatomy.

Once the protection device 600 is in position, the filter assembly 602 may be deployed from the outer sheath 604. For example, the outer sheath 604 may be proximally retracted and/or the filter assembly 602 may be distally advanced. Radiopaque markers, for example on the filter assembly 602 can help determine when the filter assembly 602 achieves a deployed state. Differential longitudinal movement of the filter assembly 602 and the outer sheath 604 can cease upon full or appropriate deployment of the filter assembly 602. Apposition of the filter assembly 602 with sidewalls of the left subclavian artery 616 can be verified, for example using radiopaque fluid or contrast media. Radiopaque fluid may be provided through the inner member 606. If the radiopaque fluid is able to flow between the frame of the filter assembly 602 and the sidewalls of the left subclavian artery 616, then the filter assembly 602 may be improperly positioned (e.g., indicative of inadequate deployment, inadequate sizing, calcium, etc.). The filter assembly 602 may be retracted back into the outer sheath 604 and redeployed, or a different protection device may be used.

As shown in FIG. 6A, during positioning of the protection device 600, the inner member 606 may distally extend from the filter assembly 602 into the aortic arch 610. As shown in FIG. 6B, the inner member 606 may be proximally retracted as indicated by the arrow 626 so that the aortic arch 610 is free or substantially free of any equipment involved in protecting the left subclavian artery 616 and/or the left vertebral artery 624. Radiopaque markers (e.g., on the inner member 606, the outer sheath 604, the filter assembly 602) and/or radiopaque fluid or contrast media can confirm the position of the inner member 606 before, during, and/or after proximal retraction of the inner member 606. Radiopaque fluid may be provided through the inner member 606. In embodiments in which the protection device lacks an inner member, retraction of an inner member is moot.

The inner member 606 may be retracted to a position suitable for monitoring or sensing blood pressure. For example, a blood pressure monitoring device can be connected in fluid communication to the inner member 606 (e.g., using a luer fitting). In embodiments in which the protection device lacks an inner member, blood pressure may be monitored or sensed by connecting a blood pressure monitoring device to the outer sheath 604.

With the protection device 600 in place, the filter assembly 602 deployed, and the inner member 606 retracted, the user or a different user can perform an endovascular procedure (e.g., TAVI, TAVR, TAMI, TAMR, SAVR, other surgical valve repair, implantation, or replacement, cardiac ablation, cardiac bypass surgery, etc.). If the endovascular procedure accesses the heart via the aortic arch 610, such access is not impeded by the protection device 600. During the endovascular procedure, any embolic material that is dislodged or generated may be carried by blood into the left subclavian artery 616. The blood may continue to flow through the filter assembly 602 (e.g., through pores in a film of the filter assembly 602), but the embolic material is trapped or captured such that the embolic material is inhibited or prevented from continuing to flow through the left subclavian artery 616, into the left vertebral artery 624, and thus into the cerebral vasculature.

Once the endovascular procedure is complete, or at any appropriate point during the endovascular procedure, the filter assembly 602 may be retracted back into the outer sheath 604 (e.g., by distally advancing the outer sheath 604 and/or by proximally retracting the filter assembly). The action to resheathe the filter assembly 602 may by opposite to the action to unsheathe the filter assembly 602 (e.g., retraction of a slider and advancement of the slider, respectively) or may be a completely different action. The inner member 606 may be distally advanced before, during, or after resheathing the filter assembly 602. Radiopaque markers, for example on the filter assembly 602 can help determine when the filter assembly 602 achieves a compressed state. Differential longitudinal movement of the filter assembly 602 and the outer sheath 604 can cease upon full or appropriate capture of the filter assembly 602. Radiopaque fluid may be provided through the inner member 606. Embolic material trapped in the filter assembly 602 may also be captured by the resheathing process. Once the protection device 600 is in a compressed state, the protection device 600 may be proximally retracted out of the left subclavian artery 616.

The protection devices described herein may be used alone or in combination with other protection devices. For example, a second protection device as described herein may be advanced via the right subclavian artery and positioned in the innominate artery, providing protection to the right carotid artery and the right vertebral artery. For another example, an aortic arch filter or deflector such as the Embrella Embolic Deflector System, the TriGuard embolic protection system, or the like may be placed across the great branch artery ostia and/or apposing sidewalls of the aortic arch upstream of at least one of the great branch artery ostia.

Figure 7:
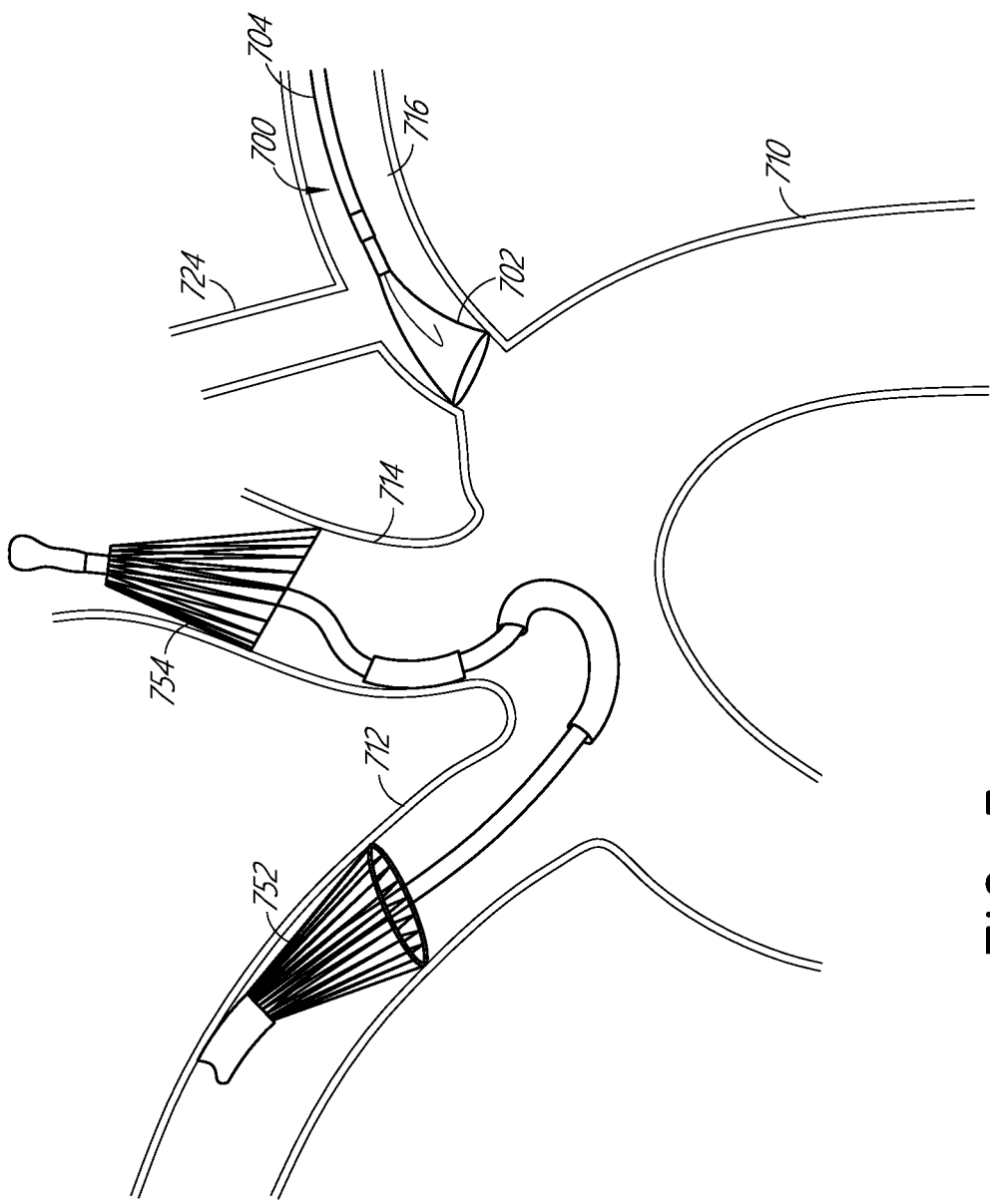
FIG. 7 illustrates an example distal portion of a protection device in a deployed state in vasculature in combination with a second protection device.

For another example, the filter systems and methods described in U.S. Pat. No. 8,876,796 can be used in combination with the protection devices described herein to further protect the cerebral vasculature during an endovascular procedure. FIG. 7 illustrates an example distal portion of a protection device 700 in a deployed state in the left subclavian artery in combination with a second protection device. To protect the right common carotid artery and the right vertebral artery (both branching downstream from the innominate artery 712) and the left common carotid artery 714 during endovascular procedures, a filter system as described in U.S. Pat. No. 8,876,796 enters the aorta 710 from the innominate artery 712. A distal rear-facing filter assembly 754 may be deployed in the left common carotid artery 714 and a proximal front-facing filter 752 may be deployed in the innominate artery 712. FIG. 7 also illustrates a protection device 700 including a filter assembly 702 deployed from an outer sheath 704 in the left subclavian artery upstream of the left vertebral artery 724, for example similar to the procedure described with respect to FIG. 6B. The filter assemblies 702, 752, 754 can inhibit or prevent embolic material from entering cerebral vasculature through any of the left vertebral artery 724, the right vertebral artery, the right common carotid artery, and the left common carotid artery 714.

Figure 8:
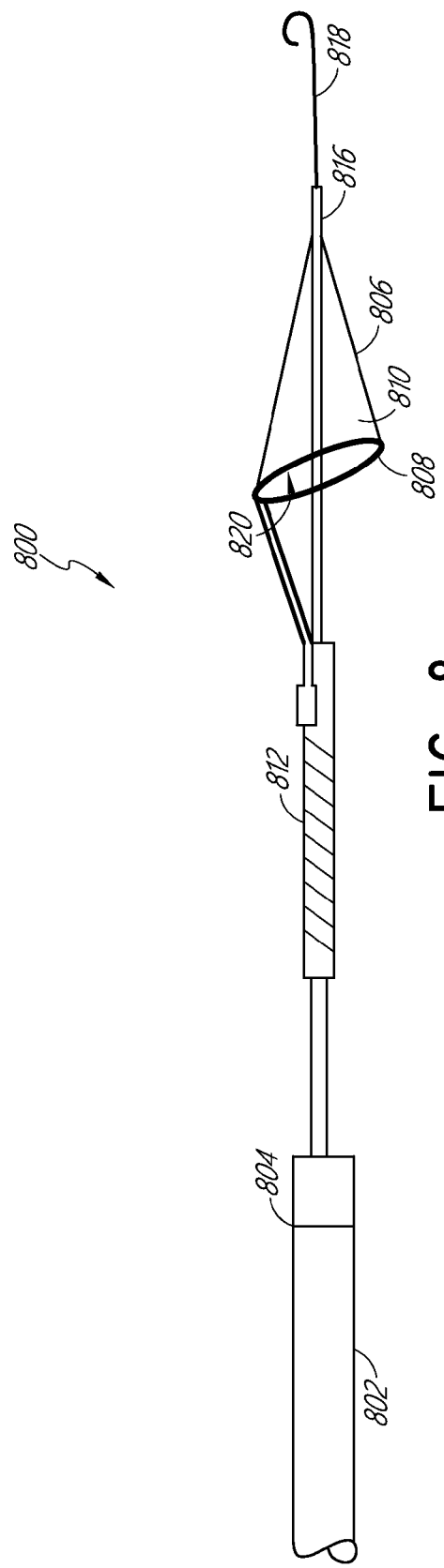
FIG. 8 illustrates an example distal portion of a protection device in a deployed state.

FIG. 8 illustrates an example distal portion 800 of a protection device in a deployed state. In contrast to the distal portions 204, 400, etc. described herein that comprise a distal-facing filter assembly, the distal portion 800 comprises a proximal or rear-facing filter assembly 806. Other aspects of the distal portion 800 may be similar to the distal portions of other protection devices described herein.

The distal portion 800 comprises an outer sheath 802 (e.g., the outer sheath 210), a radiopaque marker band 804, a filter assembly 806 (e.g., the filter assembly 218), an inner member 816 (e.g., the inner member 220), and a slotted coupler 812. One or more of the illustrated features may optionally be omitted from the distal portion 800, for example to reduce cost, to reduce complexity, to remove features not used, etc. The addition of features not illustrated in FIG. 8 is also possible.

The outer sheath 802 may include a curvature and/or be steerable, for example to turn a distal end of the distal portion 800 from the left subclavian artery into the left vertebral artery. For example, the outer sheath 802 may include one or more features described with respect to the left common carotid artery filter assemblies in U.S. Pat. No. 8,876,796. The distal end of the outer sheath 802 may have a soft atraumatic tip. The slotted coupler 812, which couples wires of the frame 808 of the filter assembly 806 to a filter wire, for example as described with respect to any of the coupling mechanisms described herein, may comprise slots to aid the slotted coupler 812 in bending (e.g., into the left vertebral artery). The wires of the frame 808 may form an inclined strut connecting the open end of the filter assembly 806 to the slotted coupler 812, which can help to radially compress the filter assembly 806 upon interaction with outer sheath 802.

The radiopaque marker 804 may be proximate to the distal end of the outer sheath 802 to help guide the distal end of the outer sheath 802 into a delivery location (e.g., the left vertebral artery). The radiopaque marker 804 may be positioned to aid a user in determining a deployed position of the filter assembly 806, for example accounting for foreshortening upon radial expansion. Once the radiopaque marker 804 is aligned with a target location or some distance proximal or distal to the target location, the filter assembly 806 can be deployed, or the distal portion 800 may be advanced or retracted a certain distance before the filter assembly 806 is deployed. As described with respect to the radiopaque marker 404, the radiopaque marker 804 may be used as a landmark with reference to the radiopaque marker 224*b*, for example to determine a degree of deployment of the filter assembly 602. The radiopaque marker 804 may be omitted (e.g., by using a radiopaque portion of the filter assembly 806).

In a delivery state, which may appear the same as the delivery state of the distal portion 400 illustrated in FIG. 4A, the distal portion 800 is radially compact, which can facilitate navigation through vasculature (e.g., through vasculature of the arm). As described herein, the outer sheath 802 and the filter assembly 806 are longitudinally movable relative to each other. When a position of the filter assembly 806 is distal to a position of the outer sheath 802 (e.g., due to proximal retraction of the outer sheath 802 and/or distal advancement of the filter assembly 806 via the filter wire), the outer sheath 802 exits the distal end of the outer sheath 802 and self-expands to the deployed state illustrated in FIG. 8. The inner member 816 may be movable independent of the outer sheath 802 and the filter assembly 806. In the deployed state, the filter assembly 806 can inhibit embolic material from entering cerebral vasculature (e.g., by filtering blood flowing in the left vertebral artery).

The filter assembly 806 comprises a support element or frame 808 and a filter element 810. The frame 808 generally provides expansion support to the filter element 810 in the expanded state. In the expanded state, the filter element 810 is configured to filter fluid (e.g., blood) flowing through the filter element 810 and to inhibit or prevent particles (e.g., embolic material) from flowing through the filter element 810 by capturing the particles in the filter element 810.

The frame 808 is configured to engage or appose the inner walls of a lumen in which the distal portion 800 is expanded. The frame 808 may comprise or be constructed of, for example, nickel titanium (e.g., nitinol), nickel titanium niobium, chromium cobalt (e.g., MP35N, 35NLT), copper aluminum nickel, iron manganese silicon, silver cadmium, gold cadmium, copper tin, copper zinc, copper zinc silicon, copper zinc aluminum, copper zinc tin, iron platinum, manganese copper, platinum alloys, cobalt nickel aluminum, cobalt nickel gallium, nickel iron gallium, titanium palladium, nickel manganese gallium, stainless steel, combinations thereof, and the like. The frame 808 may comprise a wire (e.g., having a round (e.g., circular, elliptical) or polygonal (e.g., square, rectangular) cross-section). For example, in some embodiments, the frame 808 comprises a straight piece of nitinol wire shape set into a circular or oblong hoop or hoop with one or two straight legs running longitudinally along or at an angle to the longitudinal axis of the distal portion 800. At least one of the straight legs may be coupled to a filter wire. The straight legs may be on a long side of the filter assembly 806 (e.g., the top side as illustrated in FIG. 8) and/or on a short side of the filter assembly 806 (e.g., the bottom side as illustrated in FIG. 8). The frame 808 forms a shape of an opening 820 of the filter assembly 806. The opening 820 may be circular, elliptical, or any shape that can appropriately appose sidewalls of a vessel such as the left subclavian artery or the left vertebral artery. The opening 820 faces proximally, in contrast to distal-facing devices described herein.

The frame 808 may include a radiopaque marker such as a small coil to aid in visualization under fluoroscopy. In some embodiments, the frame may not comprise a shape other than a hoop, for example a spiral. In some embodiments, the filter assembly 806 may not include or be substantially free of a frame.

In some embodiments, the frame 808 and the filter element 810 form an oblique truncated cone having a non-uniform or unequal length around and along the length of the filter assembly 806. In such a configuration, along the lines of a windsock, the filter assembly 806 has a larger opening 820 (upstream) diameter (e.g., proximate to the filter wire) and a reduced ending (downstream) diameter.

The filter element 810 comprises pores configured to allow blood to flow through the filter element 810, but that are small enough to inhibit prevent particles such as embolic material from passing through the filter element 810. The filter element 810 may comprise a polymer (e.g., polyurethane, PTFE) film mounted to the frame 806. The filter element may have a thickness between about 0.0001 inches and about 0.03 inches (e.g., no more than about 0.0001 inches, about 0.001 inches, about 0.005 inches, about 0.01 inches, about 0.015 inches, about 0.02 inches, about 0.025 inches, about 0.03 inches, ranges between such values, etc.).

The polymer film may comprise a plurality of pores or holes or apertures extending through the film. The polymer film may be formed by weaving or braiding filaments or membranes and the pores may be spaces between the filaments or membranes. The filaments or membranes may comprise the same material or may include other materials (e.g., non-polymer materials such as metal, alloys such as nitinol, stainless steel, etc.). The pores of the filter element 810 are configured to allow fluid (e.g., blood) to pass through the filter element 810 and to resist the passage of embolic material that is carried by the fluid. The pores can be circular, elliptical, square, triangular, or other geometric shapes. Certain shapes such as an equilateral triangular, squares, and slots may provide geometric advantage, for example restricting a part larger than an inscribed circle but providing an area for fluid flow nearly twice as large, making the shape more efficient in filtration verses fluid volume. The pores may be laser drilled into or through the filter element 810, although other methods are also possible (e.g., piercing with microneedles, loose braiding or weaving). The pores may have a lateral dimension (e.g., diameter) between about 1 micron (µm) and about 1 mm (e.g., about 1 µm, about 5 µm, about 10 µm, about 50 µm, about 100 µm, about 150 µm, about 200 µm, about 250 µm, about 300 µm, about 800 µm, about 500 µm, about 750 µm, about 1 mm, ranges between such values, etc.). Other pore sizes are also possible.

The material of the filter element 810 may comprise a smooth and/or textured surface that is folded or contracted into the delivery state by tension or compression into a lumen. A reinforcement fabric may be added to or embedded in the filter element 810 to accommodate stresses placed on the filter element 810 during compression. A reinforcement fabric may reduce the stretching that may occur during deployment and/or retraction of the filter assembly 806. The reinforcement material could comprise, for example, a polymer and/or metal weave to add localized strength. The reinforcement material could be imbedded into the filter element 810 to reduce thickness. For example, imbedded reinforcement material could comprise a polyester weave mounted to a portion of the filter element 810 near the longitudinal elements of the frame 808 where tensile forces act upon the frame 808 and filter element 810 during deployment and retraction of the filter assembly 806 from the outer sheath 802.

A fluid (e.g., blood) flows through the opening 820 and passes through the pores in the filter element 810, while the filter element 810 traps particles (e.g., embolic material) to inhibit or prevent passage to a location downstream of the filter assembly 806 such as the cerebral vasculature.

The distal portion 800 is illustrated with a guidewire 818 extending through a lumen of the inner member 816, indicative that the lumen of the inner member 816 may be used to guide a protection device to a location by tracking over the guidewire 818.

Figure 9A:
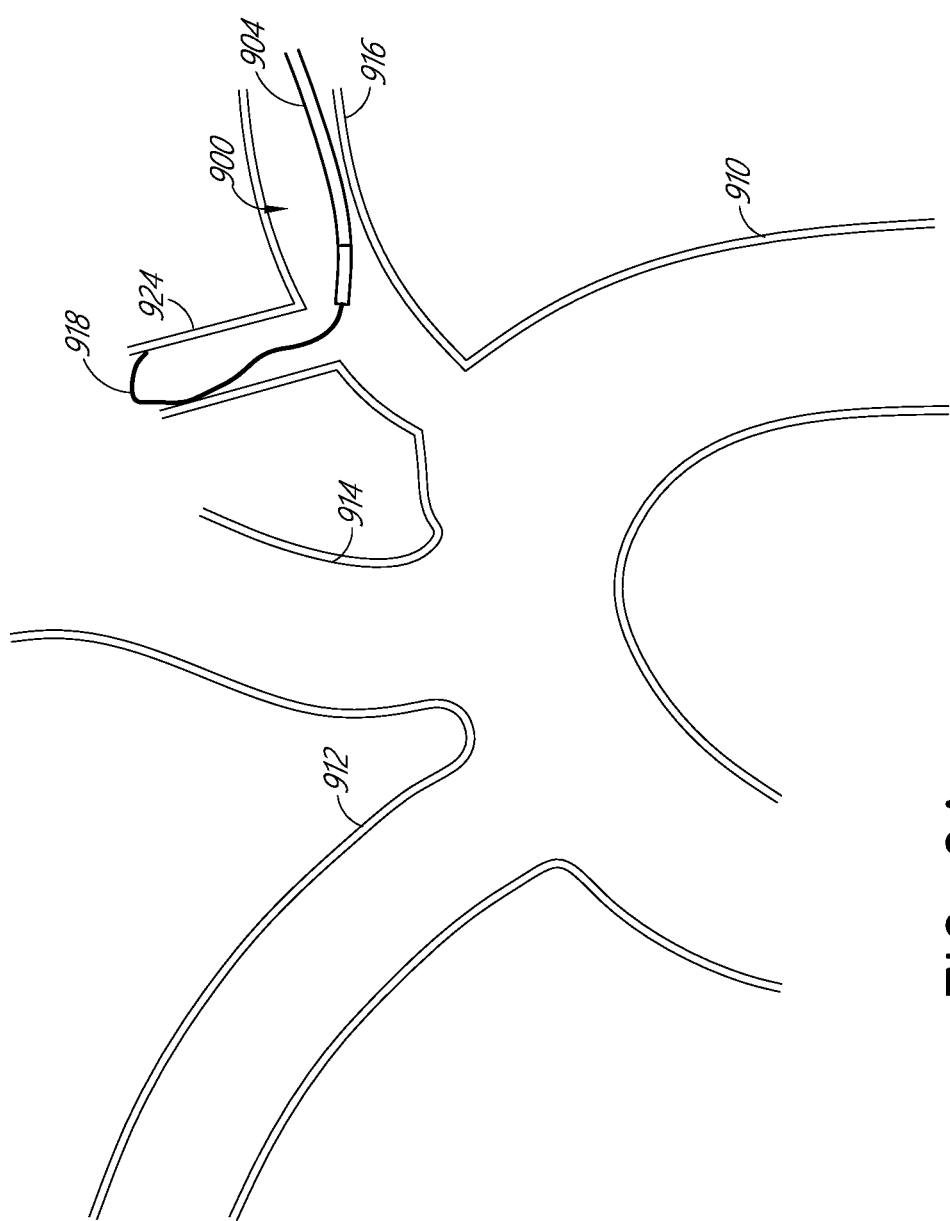
FIG. 9A illustrates the example distal portion of FIG. 9A in a delivery state in vasculature.
Figure 9B:
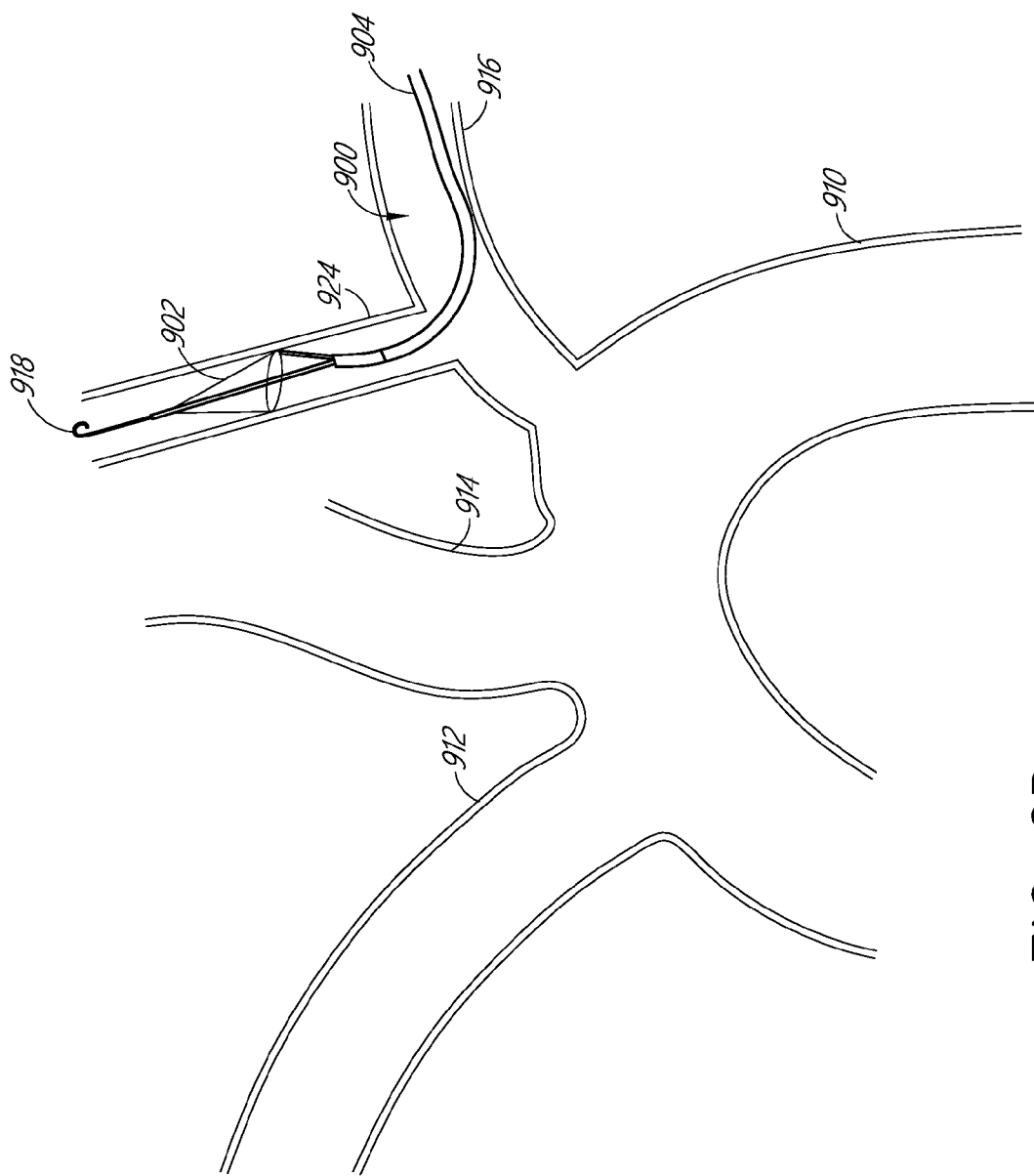
FIG. 9B illustrates the example distal portion of FIG. 9A in a deployed state in the vasculature.

FIGS. 9A and 9B illustrate method of using an example distal portion of a protection device 900 in a deployed state in vasculature. A user would like to protect cerebral vasculature (e.g., the left vertebral artery 924) from embolic debris during an endovascular procedure such as TAVI. The user has decided to place the filter assembly 902 in the left vertebral artery 924. The user may choose a protection device 900 comprising a proximal-facing filter assembly 902 having a diameter between about 2 mm and about 4.5 mm. The protection device 900 may be packaged in a sterile coiled packaging. The protection device 900 may comprise an outer sheath 904 having a diameter of about 5 Fr (approximately 1.67 mm). The outer sheath 904 may include a curvature, for example complementing the size and orientation of the filter assembly 902. The outer sheath 904 may be steerable (e.g., a pullwire-controlled sheath).

Lumens of the protection device 900, for example a lumen of the outer sheath 904 and a lumen of an inner member, may be flushed (e.g., using saline) once or several times before, during, and/or after the procedure. The filter assembly 902 of the protection device 900 may be flushed and/or submerged (e.g., in a bowl of saline). Flushing and/or submerging of the filter assembly 902 may be with the filter assembly 902 in the outer sheath 904 (e.g., in the compressed state) and/or with the filter assembly 902 out of the outer sheath 904 (e.g., in the deployed state). If the filter assembly 902 is flushed and/or submerged in the deployed state, the filter assembly 902 may be compressed into the outer sheath 904 before use.

An artery in the left arm is accessed, for example using a 5 Fr introducer. A guidewire 918 (e.g., having a diameter between about 0.014 inches and about 0.25 inches, preferably on the smaller side in view of intended navigation to the relatively small left vertebral artery 924) is steered, traversing retrograde to blood flow, into or towards the left subclavian artery 916. A proximal end of the guidewire 918 may be inserted into a distal end of the protection device 900, for example into a distal end of an inner member. The protection device 900 may be tracked over the guidewire 918 until the distal end of the protection device 900 extends beyond a distal end of the introducer. The guidewire 918 may be advanced at least about 6 cm distal to the distal end of the protection device 900. FIG. 9A shows the guidewire 918 in position in the left vertebral artery 924 with the protection device 900 being tracked over the guidewire 918. The guidewire 918 may comprise a pigtail or floppy distal end, for example to make the guidewire 918 atraumatic or more atraumatic.

The protection device 900 may be tracked or distally advanced over the guidewire 918 until the distal end of the protection device 900 is at a desired location such as in the left vertebral artery 924. Tracking of the protection device 900 may be under fluoroscopy, for example using radiopaque markers (e.g., at a distal end of the outer sheath 904 and/or an inner member) and/or radiopaque fluid or contrast media. Radiopaque fluid may be provided through an inner member. The protection device 900 is preferably positioned so that the filter assembly 902 is downstream of the left vertebral artery 924 ostium so that the filter assembly 902 can inhibit or prevent embolic material from entering the cerebral vasculature through the left vertebral artery 924. The location in the left vertebral artery 924 is preferably free or substantially free of calcium and straight or substantially straight. Positioning based on available anatomy that is not as preferred is also possible.

Once the protection device 900 is in position, the filter assembly 902 may be deployed from the outer sheath 904. For example, the outer sheath 904 may be proximally retracted and/or the filter assembly 902 may be distally advanced. Radiopaque markers, for example on the filter assembly 902 can help determine when the filter assembly 902 achieves a deployed state. Differential longitudinal movement of the filter assembly 902 and the outer sheath 904 can cease upon full or appropriate deployment of the filter assembly 902. Apposition of the filter assembly 902 with sidewalls of the left subclavian artery 916 can be verified, for example using radiopaque fluid or contrast media. Radiopaque fluid may be provided through an inner member. If the radiopaque fluid is able to flow between the frame of the filter assembly 902 and the sidewalls of the left vertebral artery 924, then the filter assembly 902 may be improperly positioned (e.g., indicative of inadequate deployment, inadequate sizing, calcium, etc.). The filter assembly 902 may be retracted back into the outer sheath 904 and redeployed, or a different protection device may be used.

If the protection device 900 comprises an inner member, the inner member may extend downstream in the left vertebral artery 924. Whether the inner member is retracted or not, the aortic arch 910 is free or substantially free of any equipment involved in protecting the left vertebral artery 924.

An inner member may be retracted to a position suitable for monitoring or sensing blood pressure. For example, a blood pressure monitoring device can be connected in fluid communication to an inner member (e.g., using a luer fitting). The distal end of an inner member may be in the left vertebral artery 924 to monitor pressure in the left vertebral artery 924. The distal end of an inner member may be in the left subclavian artery 916 to monitor pressure in the left subclavian artery 916. In embodiments in which the protection device lacks an inner member, blood pressure may be monitored or sensed by connecting a blood pressure monitoring device to the outer sheath 904. The distal end of the outer sheath 904 may be in the left vertebral artery 924 (e.g., as illustrated in FIG. 9B) to monitor pressure in the left vertebral artery 924. The distal end of the outer sheath 904 may be in the left subclavian artery 916 to monitor pressure in the left subclavian artery 916.

With the protection device 900 in place and the filter assembly 902 deployed, the user or a different user can perform an endovascular procedure (e.g., TAVI, TAVR, TAMI, TAMR, SAVR, other surgical valve repair, implantation, or replacement, cardiac ablation, cardiac bypass surgery, etc.). If the endovascular procedure accesses the heart via the aortic arch 910, such access is not impeded by the protection device 900. During the endovascular procedure, any embolic material that is dislodged or generated may be carried by blood into the left vertebral artery 924. The blood may continue to flow through the filter assembly 902 (e.g., through pores in a film of the filter assembly 902), but the embolic material is trapped or captured such that the embolic material is inhibited or prevented from continuing to flow through the left vertebral artery 924 and thus into the cerebral vasculature.

Once the endovascular procedure is complete, or at any appropriate point during the endovascular procedure, the filter assembly 902 may be retracted back into the outer sheath 904 (e.g., by distally advancing the outer sheath 904 and/or by proximally retracting the filter assembly). The action to resheathe the filter assembly 902 may by opposite to the action to unsheathe the filter assembly 902 (e.g., retraction of a slider and advancement of the slider, respectively) or may be a completely different action. Radiopaque markers, for example on the filter assembly 902 can help determine when the filter assembly 902 achieves a compressed state. Differential longitudinal movement of the filter assembly 902 and the outer sheath 904 can cease upon full or appropriate capture of the filter assembly 902. Radiopaque fluid may be provided through an inner member. Embolic material trapped in the filter assembly 902 may also be captured by the resheathing process. Once the protection device 900 is in a compressed state, the protection device 900 may be proximally retracted out of the left vertebral artery 924.

Figure 10:
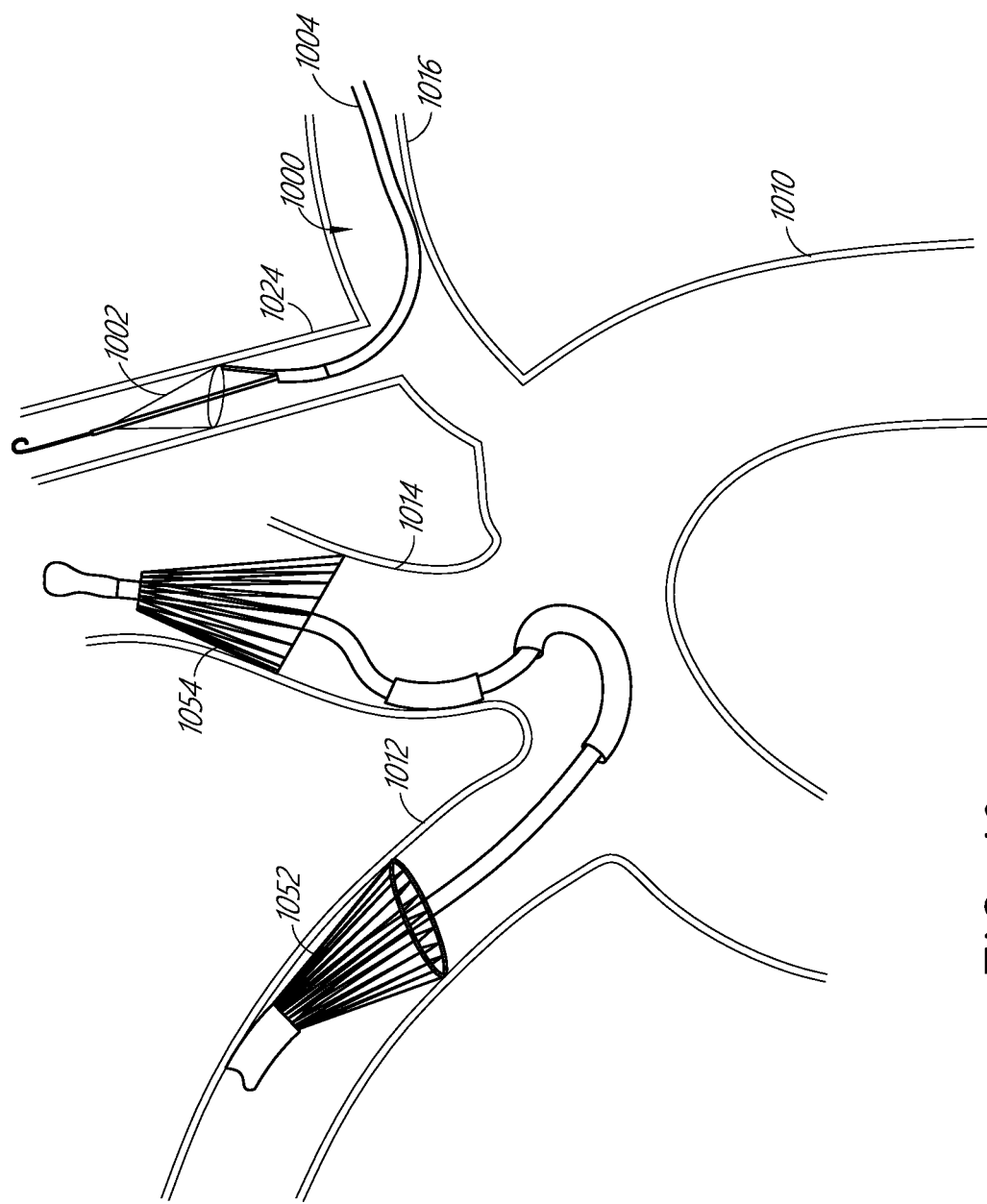
FIG. 10 illustrates another example distal portion of a protection device in a deployed state in vasculature in combination with a second protection device.

FIG. 10 illustrates an example distal portion of a protection device 1000 in a deployed state in vasculature in combination with a second protection device such as the filter systems and methods described in U.S. Pat. No. 8,876,796. To protect the right common carotid artery and the right vertebral artery (both branching downstream from the innominate artery 1012) and the left common carotid artery 1014 during endovascular procedures, a filter system as described in U.S. Pat. No. 8,876,796 enters the aorta 1010 from the innominate artery 1012. A distal rear-facing filter assembly 1054 may be deployed in the left common carotid artery 1014 and a proximal front-facing filter 1052 may be deployed in the innominate artery 1012. FIG. 10 also illustrates a protection device 1000 including a filter assembly 1002 deployed from an outer sheath 1004 in the left vertebral artery 1024, for example similar to the procedure described with respect to FIG. 9B. The filter assemblies 1002, 1052, 1054 can inhibit or prevent embolic material from entering cerebral vasculature through any of the left vertebral artery 1024, the right vertebral artery, the right common carotid artery, and the left common carotid artery 1014. Embolic material may be allowed to flow downstream of the left subclavian artery 1016.

In any of the embodiments described herein, the filter assembly may be detached from the protection device, and the remainder of the protection device removed, leaving the filter assembly behind. The filter assembly can remain in the location permanently or can be retrieved by snaring with a retrieval catheter, for example following a post procedure treatment duration (e.g., at least one day, one week, three weeks, five weeks, or more, depending upon the clinical circumstances). Subjects receiving an indwelling filter assembly may be administered any of a variety of thrombolytic or anticoagulant therapies, including tissue plasminogen activator, streptokinase, coumadin, heparin, combinations thereof, and the like.

FIG. 11 illustrates another example distal portion of a protection device 1100 in a deployed state in vasculature. The protection device 1100 is shown as deployed across the ostium of the left subclavian artery 1116, and may extend slightly into the aorta 1110. The protection 1100 device may be slightly downstream of the ostium of the left subclavian artery 1116, but close to the ostium is preferred. Blood can flow through the protection device 1100, but the protection device 1100 deflects embolic material away from the left subclavian artery 1116. The embolic material may flow into the descending aorta and towards the legs. Redundant vasculature, vasculature length, vasculature diameter, natural thrombolytic agents, and the like allow embolic material to flow to the legs causing less harm than if the same embolic material flowed to the cerebral vasculature. A deflector may advantageously be smaller than a filter, which can reduce size of the protection device 1100. A smaller protection device 1100 may be easier to route through vasculature, allow multiple catheters to be used, etc. A deflector may advantageously reduce a user's worry about capturing the embolic material.

FIG. 12A illustrates an example protection device 1200. The protection device 1200 is in a deployed state in FIG. 12A. The protection device 1200 comprises an outer sheath 1204 and a deflector assembly 1202. The deflector assembly 1202 comprises a frame 1208 and a deflector film 1206. The deflector film 1206 may be planar or substantially planar, convex, concave, saddle-shaped, or any other appropriate shape. The deflector film 1206 may comprise a membrane such as a polymer (e.g., polyurethane, PTFE) film, a woven mesh of strands (e.g., comprising one or more of shape memory (e.g., nitinol), metal, polymer, etc.), combinations thereof, and the like mounted to the frame 1208. The deflector film 1206 may have similar properties to the filter element 410 and/or other films described herein (e.g., comprising pores configured to allow blood to flow through the deflector film 1206 but to resist the passage of embolic material that is carried by the fluid). In contrast to the filter elements, the deflector assembly 1202 comprises the deflector film 1206 on a distal surface (e.g., like a potato masher) rather than having an open distal mouth and the filter element in a generally frustoconical shape extending proximally from the mouth. The frame 1208 comprises two wires 1210a, 1210b extending proximal to the deflector film 1206. The wires 1210a, 1210b may be coupled to a deployment wire, deployment tube, etc., for example as described herein with respect to filter assembly wires. More or fewer wires are also possible. The deflector assembly 1202 may be collapsible into a compressed or delivery state at least partially in the outer sheath 1204. The deflector assembly 1202 may have a diameter between about 8 mm and about 14 mm (e.g., about 8 mm, about 9 mm, about 10 mm, about 11 mm, about 12 mm, about 13 mm, about 14 mm, ranges between such values, and the like). Diameters smaller than about 8 mm and larger than about 14 mm are also possible, for example depending on anatomy of a subject, location of placement, and the like. The deflector assembly 1202 may be circular, oval, ellipsoid, egg-shaped, other arcuate shapes, polygonal shapes, combinations thereof, and the like.

FIG. 12B illustrates another example protection device 1250. The protection device 1250 is in a deployed state in FIG. 12B. The protection device 1250 comprises an outer sheath 1254 and a deflector assembly 1252. The deflector assembly 1252 comprises a frame 1258 and a deflector film 1256. The deflector film 1256 may be planar or substantially planar, convex, concave, saddle-shaped, or any other appropriate shape. The deflector film 1256 may comprise a membrane such as a polymer (e.g., polyurethane, PTFE) film mounted to the frame 1258. The deflector film 1256 may have similar properties to the filter element 410 and/or other films, a woven mesh of strands (e.g., comprising one or more of shape memory (e.g., nitinol), metal, polymer, etc.), combinations thereof, and the like described herein (e.g., comprising pores configured to allow blood to flow through the deflector film 1256 but to resist the passage of embolic material that is carried by the fluid). The deflector assembly 1252 may be collapsible into a compressed or delivery state at least partially in the outer sheath 1254, for example by folding like butterfly wings along an axis 1260, the axis 1260 being a distal end of the deflector assembly 1252. The frame 1258 comprises two wires 1264a, 1264b extending proximal to the deflector film 1256 and on each side of the axis 1260. The wires 1264a, 1264b may be coupled to a deployment wire, deployment tube, etc., for example as described herein with respect to filter assembly wires. More or fewer wires are also possible. The deflector film 1256, as well as other deflector films described herein, may comprise an aperture 1262 configured to allow the use of an inner member, for example as described herein. The deflector assembly 1252 may have a lateral length between about 9 mm and about 18 mm (e.g., about 9 mm, about 10 mm, about 11 mm, about 12 mm, about 13 mm, about 14 mm, about 15 mm, about 16 mm, about 17 mm, about 18 mm, ranges between such values, and the like). Lateral lengths smaller than about 9 mm and larger than about 18 mm are also possible, for example depending on anatomy of a subject, location of placement, and the like. The deflector assembly 1252 may have a lateral width between about 8 mm and about 14 mm (e.g., about 8 mm, about 9 mm, about 10 mm, about 11 mm, about 12 mm, about 13 mm, about 14 mm, ranges between such values, and the like). Lateral lengths smaller than about 8 mm and larger than about 14 mm are also possible, for example depending on anatomy of a subject, location of placement, and the like. The deflector assembly 1252 can be generally rectangular (length greater than width), square (length and width substantially equal), trapezoidal, rhomboid, other polygonal shapes, arcuate shapes, combinations thereof, and the like.

The deflector films 1206, 1256 may be placed across the ostium of the left subclavian artery, as shown in FIG. 11. The deflector protection devices may be used alone or in combination with other protection devices as described herein. For example, the filter systems and methods described in U.S. Pat. No. 8,876,796 can be used in combination with the protection devices 1100, 1200, 1250 described herein to further protect the cerebral vasculature during an endovascular procedure (e.g., as understood by a combination of FIG. 7 with the protection device 700 replaced by a deflector device as shown in FIG. 11).

FIGS. 13A-13D illustrate another example protection device 1300. The protection device 1300 is in a first alternative delivery state in FIG. 13A. The protection device 1300 comprises an outer sheath 1308, a deflector assembly comprising a deflector film 1302, and an inner member 1310. The deflector film 1302 is coupled to a distal end of the outer sheath 1308 at a connection point 1304 and is coupled to a distal end of the inner member 1310 at a connection point 1306. The deflector film 1302 may have similar properties to the filter element 410 and/or other films, a woven mesh of strands (e.g., comprising one or more of shape memory (e.g., nitinol), metal, polymer, etc.), combinations thereof, and the like described herein (e.g., comprising pores configured to allow blood to flow through the deflector film 1302 but to resist the passage of embolic material that is carried by the fluid). Use of the state of FIG. 13A for delivery may advantageously provide the inner element for the length of the protection device, for example inhibiting or preventing a guidewire from interacting with the deflector film 1302.

In FIG. 13B, the inner member 1310 is retracted proximally, as indicated by the arrow 1312. The distal end of the inner member 1310 also retracts proximally, and due to the connection point 1306, the distal portion of the deflector film 1302 in the delivery position retracts proximally and the deflector film 1302 flares radially outwardly, as indicated by the arrow 1314. FIG. 13C shows the protection device 1300 in a deployed state. Achievement of the deployed state may be indicated by alignment of or a certain distance between the connection points 1304, 1306, which may include radiopaque material (e.g., radiopaque solder or adhesive).

In the deployed state, the deflector film 1302 forms a two-layered generally frustoconical shape that may have similar properties to the filter element 410 and/or other films, a woven mesh of strands (e.g., comprising one or more of shape memory (e.g., nitinol), metal, polymer, etc.), combinations thereof, and the like described herein (e.g., comprising pores configured to allow blood to flow through the deflector film 1302 but to resist the passage of embolic material that is carried by the fluid). While the deflector film 1302 forms a generally frustoconical shape in the deployed state, the protection device 1300 is described herein as comprising a deflector assembly rather than a filter assembly because the embolic material may not ultimately be captured by the deflector film 1302. For example, the embolic material may be deflected back into the aorta if the device 1300 is returned to the first option delivery or withdrawal state (e.g., as shown in FIG. 13A), in which the embolic material may be allowed to flow to the descending aorta. For another example, the embolic material may be captured if the device 1300 is returned to the second option delivery or withdrawal state (e.g., as shown in FIG. 13D), in which the embolic material may be captured in the outer sheath 1308. The device 1300 and its components may appropriately be called a filter and/or a deflector based on the context. In an orientation forming a generally frustoconical shape such as shown in FIGS. 13B, 13C, and 13F, the deflector assembly 1302 may have a mouth diameter between about 8 mm and about 14 mm (e.g., about 8 mm, about 9 mm, about 10 mm, about 11 mm, about 12 mm, about 13 mm, about 14 mm, ranges between such values, and the like). Mouth diameters smaller than about 8 mm and larger than about 14 mm are also possible, for example depending on anatomy of a subject, location of placement, and the like.

FIG. 13D shows a maximally contracted state in which the inner member 1310 is proximally retracted until a physical limit is reached with the deflector film 1302 fully inside the outer sheath 1308. FIG. 13D may be a second alternative delivery state of the protection device 1300, which may advantageously protect the deflector film 1302 during routing during vasculature. Rather than proximally retracting the inner member 1310 to form the generally frustoconical shape of the deflector film 1302, the inner member 1310 may be distally advanced, for example as shown in FIG. 13F.

A third alternative delivery state may comprise inserting a guidewire into a distal end of the inner member 1310 in the state of FIG. 13A (e.g., using a guidewire loading tool 500) and, once the distal end of the guidewire is distal to the distal end of the inner member 1310, proximally retracting the inner member 1310 until the device is in the state of FIG. 13D with the distal end of the guidewire distal to the distal end of the outer sheath 1308 and thus the deflector film 1302. This state may provide the advantage of protecting the deflector film 1302 in the outer sheath 1308 and avoid a potential disadvantage of interaction between the guidewire and the deflector film 1302.

FIGS. 13E and 13F are cross-sectional views of the example protection device 1300 of FIGS. 13A-13D. FIG. 13E shows the device in the state of FIG. 13D. FIG. 13F illustrates the distal advancement of the inner member 1310, as indicated by the arrow 1314, forming the generally frustoconical shape of the deflector film 1302, as indicated by the arrow 1316.

Regardless of the delivery shape or advancement method, the mouth of the generally frustoconical shape is preferably across the ostium of the left subclavian artery. After performing a vascular procedure, the inner member 1310 can the fully distally advanced (e.g., to the state of FIG. 13A) such that embolic material in the deflector film 1302 is pushed into the aorta to then flow into the descending aorta. The protection device 1300 may be used alone or in combination with other protection devices as described herein. For example, the filter systems and methods described in U.S. Pat. No. 8,876,796 can be used in combination with the protection device 1300 described herein to further protect the cerebral vasculature during an endovascular procedure (e.g., as understood by a combination of FIG. 7 with the protection device 700 replaced by the deflector device 1300).

Figure 14:
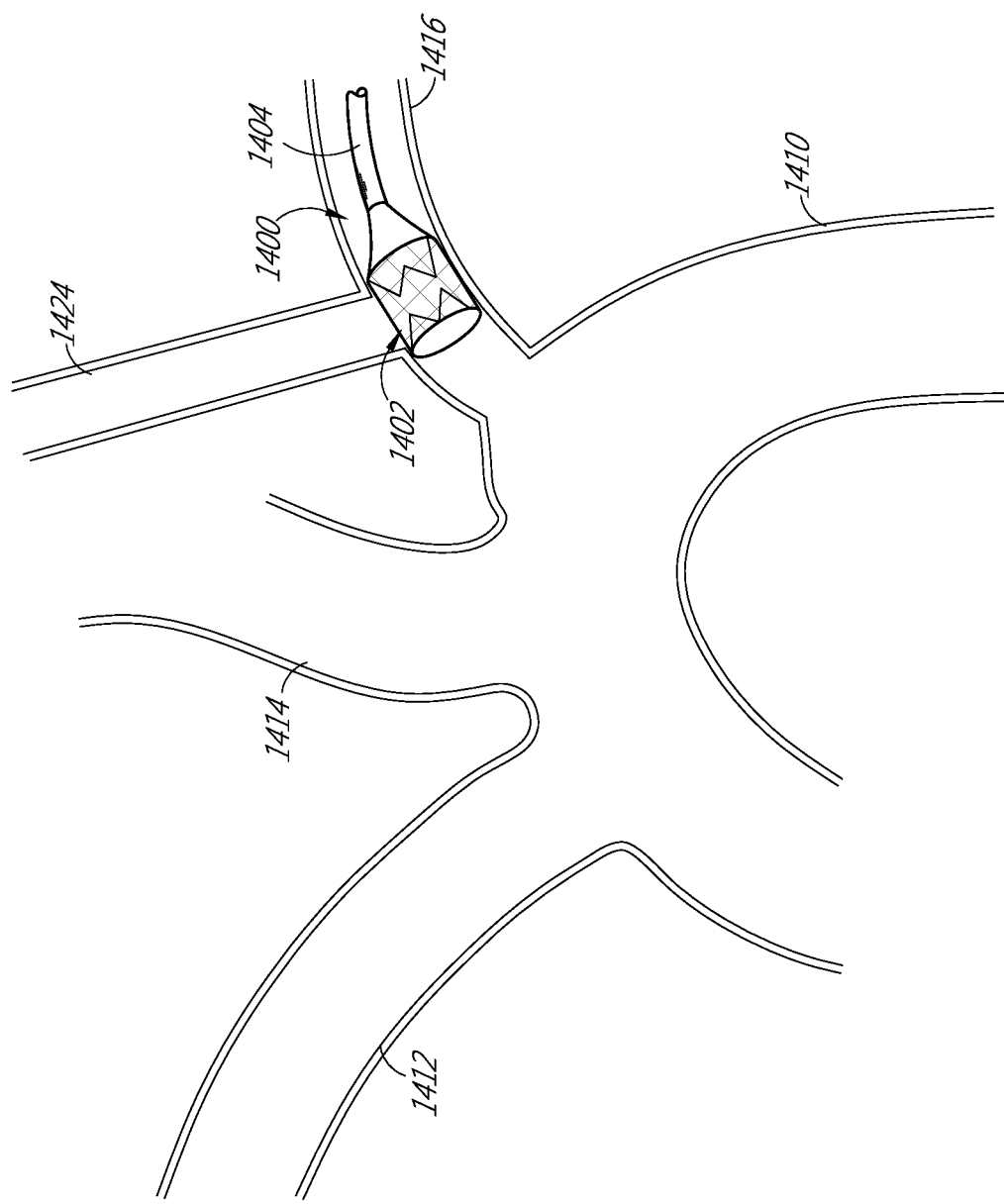
FIG. 14 illustrates another example distal portion of a protection device in a deployed state in vasculature.

FIG. 14 illustrates another example distal portion of a protection device 1400 in a deployed state in vasculature. The protection device 1400 comprises a deflector assembly 1402 and an outer sheath 1404. The protection device 1400 is shown as deployed across the ostium of the left vertebral artery 1424. The deflector assembly 1402 may extend upstream and downstream of the ostium of the left vertebral artery along the length of the left subclavian artery 1416. Blood can flow longitudinally through the deflector assembly 1402. Blood can also flow through the protection device into the left vertebral artery 1424, but the deflector assembly 1402 deflects embolic material away from the left vertebral artery 1424. The embolic material may flow longitudinally through the protection device 1400 into the portion of the left subclavian artery 1416 downstream of the ostium of the left vertebral artery 1424 and into the left arm. Redundant vasculature, vasculature length, vasculature diameter, natural thrombolytic agents, and the like allow embolic material to flow to the left arm causing less harm than if the same embolic material flowed to the cerebral vasculature. A deflector may advantageously be smaller than a filter, which can reduce size of the protection device 1400. A smaller protection device 1400 may be easier to route through vasculature, allow multiple catheters to be used, etc. A deflector may advantageously reduce a user's worry about capturing the embolic material.

FIGS. 15A-15D illustrate another example protection device 1500. The protection device 1500 may be positioned in the left subclavian artery across the ostium of the left vertebral artery similar to the protection device 1400. Referring to the deployed or expanded state of FIG. 15D, the protection device 1500 comprises an outer sheath 1504 and a deflector assembly 1502. An inner member as described herein may be used with the protection device 1500, for example extending through the deflector assembly 1502. The outer sheath 1504 may comprise, for example, a braid-reinforced polymer tube. The deflector assembly 1502 comprises a frame 1506 and a deflector film 1508. The frame 1506 may have similar properties to the frame 408 and/or other frames described herein (e.g., providing expansion support to the deflector film 1508 in the expanded state). The frame 1506 may comprise, for example, a laser-cut hypotube, a woven structure, etc. The deflector film 1508 may have similar properties to the filter element 410 and/or other films, a woven mesh of strands (e.g., comprising one or more of shape memory (e.g., nitinol), metal, polymer, etc.), combinations thereof, and the like described herein (e.g., comprising pores configured to allow blood to flow through the deflector film 1508 but to resist the passage of embolic material that is carried by the fluid). The deflector film 1508 may comprise, for example, a microporous structure comprising pores having diameters between about 60 μm and about 200 μm, and comprising a braided structure, a drilled polymer, an expanded polymer, etc. The frame 1506 comprises wires or struts 1510 extending proximal to the deflector film 1508. The wires 1510 may be coupled to a deployment wire, deployment tube, etc., for example as described herein with respect to filter assembly wires. The deflector assembly 1502 may be collapsible into a compressed or delivery state at least partially in the outer sheath 1504.

Figure 15A:
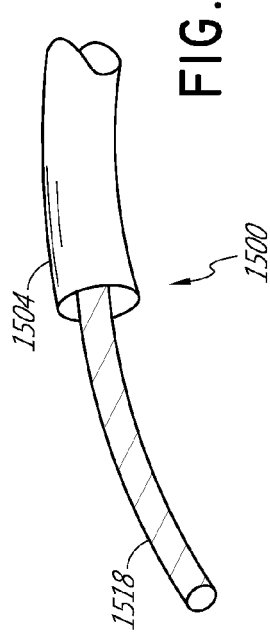
FIGS. 15A-15D illustrate another example protection device.
Figure 15B:
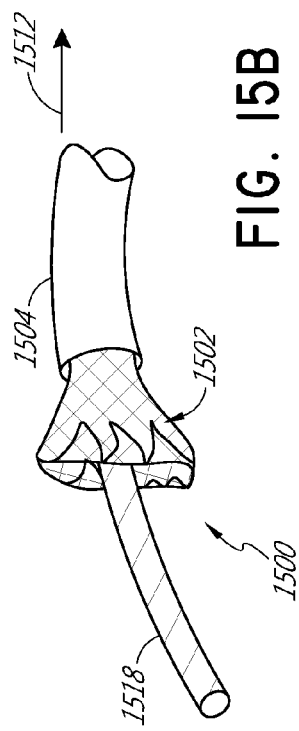
Figure 15C:
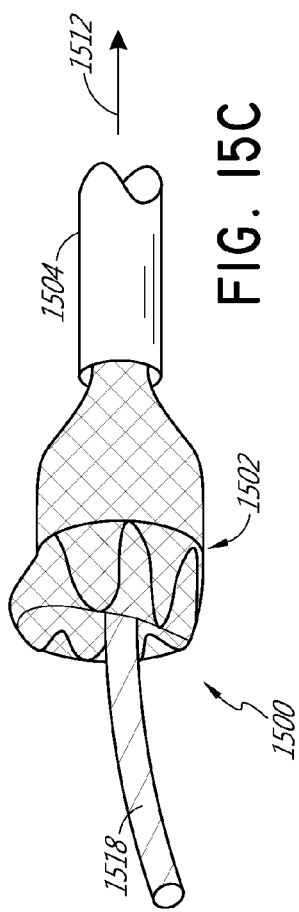
Figure 15D:
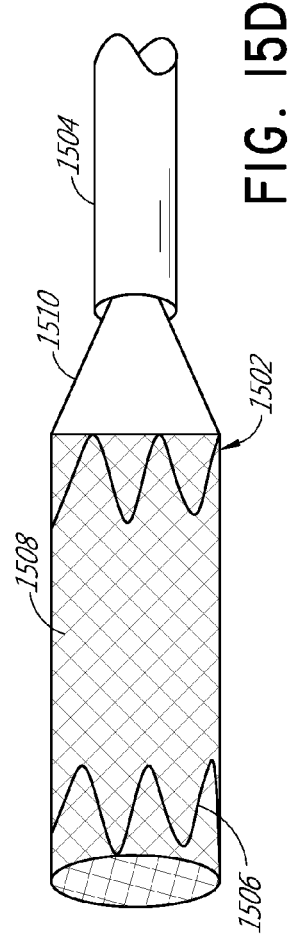

FIG. 15A shows the protection device 1500 in a delivery state in which the deflector assembly is not visible because it is in the outer sheath 1504. FIG. 15A also shows a guidewire 1518 over which the protection device 1500 can be tracked. FIG. 15B shows the outer sheath 1504 being proximally retracted, as indicated by the arrow 1512, allowing the deflector assembly 1502 to self-expand radially outwardly (e.g., due to the deflector assembly 1502 being coupled to a deployment wire that is held stationary and/or distally advanced). FIG. 15C shows further retraction of the outer sheath 1504, and the deflector assembly 1502 is fully deployed in FIG. 15D. The deflector assembly 1502 may be retracted back in the outer sheath 1504 after a vascular procedure by distally advancing the outer sheath 1504 and/or proximally retracting the deflector assembly 1502. The deflector assembly 1502 may have a diameter between about 8 mm and about 14 mm (e.g., about 8 mm, about 9 mm, about 10 mm, about 11 mm, about 12 mm, about 13 mm, about 14 mm, ranges between such values, and the like). Diameters smaller than about 8 mm and larger than about 14 mm are also possible, for example depending on anatomy of a subject, location of placement, and the like. The deflector assembly 1502 may have a cross-section that is circular (e.g., as illustrated in FIG. 15D), oval, ellipsoid, egg-shaped, other arcuate shapes, polygonal shapes, combinations thereof, and the like. The deflector assembly 1502 may have a length in an expanded state (e.g., as shown in FIG. 15D) between about 3 mm and about 16 mm (e.g., about 3 mm, about 4 mm, about 5 mm, about 6 mm, about 7 mm, about 8 mm, about 9 mm, about 10 mm, about 11 mm, about 12 mm, about 13 mm, about 14 mm, about 15 mm, about 16 mm, ranges between such values, and the like). Lengths larger than about 16 mm are also possible, for example depending on anatomy of a subject, location of placement, and the like. A deflector assembly 1502 having a length greater than a diameter of an ostium of the left vertebral artery (e.g., greater than about 6 mm) may provide stability in the left subclavian artery, for example by providing circumferential sidewall apposition proximal and/or distal to the ostium of the left vertebral artery.

Figure 16A:
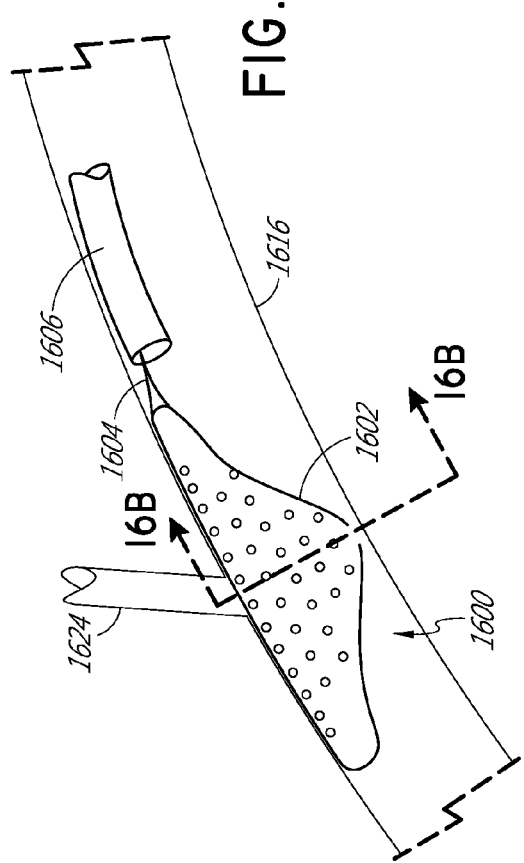
FIG. 16A illustrates another example distal portion of a protection device in a deployed state in vasculature.
Figure 16B:
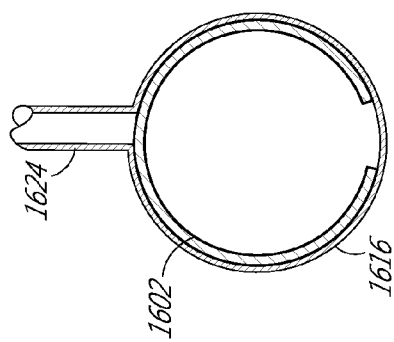
FIG. 16B is a cross-sectional view of the example distal portion of the protection device and the vasculature of FIG. 16A along the line 16B-16B of FIG. 16A.

FIG. 16A illustrates another example distal portion of a protection device 1600 in a deployed state in vasculature. FIG. 16B is a cross-sectional view of the example distal portion of the protection device 1600 and the vasculature of FIG. 16A along the line 16B-16B of FIG. 16A. The protection device 1600 is positioned in the left subclavian artery 1616 across the ostium of the left vertebral artery 1624 in a deployed state. The protection device 1600 comprises an outer sheath 1606 and a deflector assembly 1602. In contrast to the fully arcuate deflector assembly 1502, the deflector assembly 1602 is partially arcuate, as seen in FIG. 16B. An inner member as described herein may be used with the protection device 1600, for example extending through the deflector assembly 1602. The deflector assembly 1602 comprises a wire or strut 1604, which may be coupled to a deployment wire, deployment tube, etc., for example as described herein with respect to filter assembly wires. The deflector assembly 1602 may be collapsible into a compressed or delivery state at least partially in the outer sheath 1606, for example as described with respect to FIGS. 15A-15D. The deflector assembly 1602 may have a diameter between about 8 mm and about 14 mm (e.g., about 8 mm, about 9 mm, about 10 mm, about 11 mm, about 12 mm, about 13 mm, about 14 mm, ranges between such values, and the like). Diameters smaller than about 8 mm and larger than about 14 mm are also possible, for example depending on anatomy of a subject, location of placement, and the like. The deflector assembly 1502 may have a cross-section that is circular, oval, ellipsoid, egg-shaped, other arcuate shapes, polygonal shapes, combinations thereof, and the like. The deflector assembly 1502 may have a length in an expanded state (e.g., as shown in FIG. 16) between about 3 mm and about 16 mm (e.g., about 3 mm, about 4 mm, about 5 mm, about 6 mm, about 7 mm, about 8 mm, about 9 mm, about 10 mm, about 11 mm, about 12 mm, about 13 mm, about 14 mm, about 15 mm, about 16 mm, ranges between such values, and the like). Lengths larger than about 16 mm are also possible, for example depending on anatomy of a subject, location of placement, and the like. A deflector assembly 1602 having a length greater than a diameter of an ostium of the left vertebral artery (e.g., greater than about 6 mm) may provide stability in the left subclavian artery, for example by providing substantially circumferential sidewall apposition proximal and/or distal to the ostium of the left vertebral artery.

Figure 17:
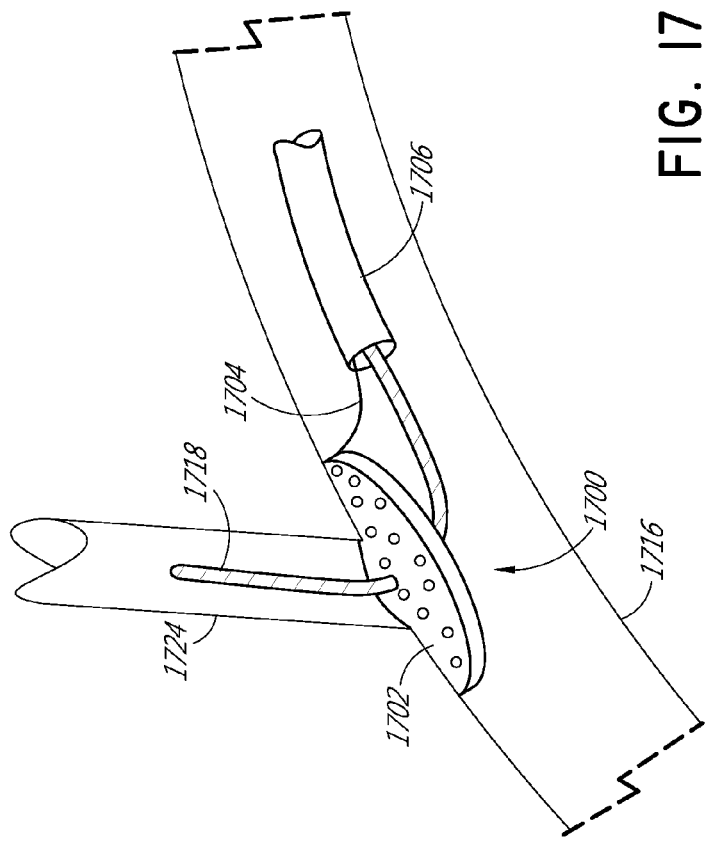
FIG. 17 illustrates another example distal portion of a protection device in a deployed state in vasculature.

FIG. 17 illustrates another example distal portion of a protection device 1700 in a deployed state in vasculature. The protection device 1700 is positioned in the left subclavian artery 1716 across the ostium of the left vertebral artery 1724 in a deployed state. The protection device 1700 comprises an outer sheath 1706 and a deflector assembly 1702. In contrast to the fully arcuate deflector assembly 1502 or the partially arcuate deflector assembly 1602, the deflector assembly 1702 is generally planar, concave, convex, saddle-shaped, or the like, and is configured to cover the ostium of the left vertebral artery 1724. An inner member as described herein may be used with the protection device 1700, for example extending through the deflector assembly 1702. The deflector assembly 1702 comprises a wire or strut 1704, which may be coupled to a deployment wire, deployment tube, etc., for example as described herein with respect to filter assembly wires. The deflector assembly 1702 may be collapsible into a compressed or delivery state at least partially in the outer sheath 1706, for example as described with respect to FIGS. 15A-15D. FIG. 17 illustrates a guidewire 1718 in the left vertebral artery 1724. The guidewire 1718 may provide circumferential orientation of the deflector assembly 1702. For example, the deflector assembly 1702 may be advanced along the guidewire 1718 such that the deflector assembly 1702 advances towards the left vertebral artery 1724. The deflector assembly 1702 may have a lateral diameter between about 3 mm and about 16 mm (e.g., about 3 mm, about 4 mm, about 5 mm, about 6 mm, about 7 mm, about 8 mm, about 9 mm, about 10 mm, about 11 mm, about 12 mm, about 13 mm, about 14 mm, about 15 mm, about 16 mm, ranges between such values, and the like). Lengths larger than about 16 mm are also possible, for example depending on anatomy of a subject, location of placement, and the like. A deflector assembly 1702 having a length greater than a diameter of an ostium of the left vertebral artery (e.g., greater than about 6 mm) may provide easier placement across the ostium of the left vertebral artery.

Combinations of filter assemblies and deflector assemblies provided herein are also possible. For example, the protection device may comprise a filter assembly (e.g., the filter assembly 218, 406) and a deflector assembly (e.g., the deflector assembly 1402, 1502, 1602, 1702) proximal to the filter assembly, for example coupled to the same deployment wire such that relative movement of the deployment wire and the outer sheath can deploy both the filter assembly and the deflector assembly. The filter assembly can filter blood proximate to the ostium of the left subclavian artery and the deflector assembly can provide a second layer of protection by deflecting any embolic material that somehow passes through the filter assembly or that forms downstream of the filter assembly from entering the left vertebral artery.

A possible advantage of the protection devices described herein may be that the delivery and retrieval system are integrated into the same catheter that stays in place during the procedure. Unloading and loading of different catheters, sheaths, or other components is therefore unnecessary. Having a system that performs both deliversy and retrieval functions can reduce procedural complexity, time, and fluoroscopy exposure time. The device is not in the aortic arch, which can reduce or eliminate the chance of interference with other catheters.

While the methods and devices described herein may be susceptible to various modifications and alternative forms, specific examples thereof have been shown in the drawings and are described in detail herein. It should be understood, however, that the inventive subject matter is not to be limited to the particular forms or methods disclosed, but, to the contrary, covers all modifications, equivalents, and alternatives falling within the spirit and scope of the various implementations described and the appended claims. Further, the disclosure herein of any particular feature, aspect, method, property, characteristic, quality, attribute, element, or the like in connection with an implementation or embodiment can be used in all other implementations or embodiments set forth herein. In any methods disclosed herein, the acts or operations can be performed in any suitable sequence and are not necessarily limited to any particular disclosed sequence and not be performed in the order recited. Various operations can be described as multiple discrete operations in turn, in a manner that can be helpful in understanding certain embodiments; however, the order of description should not be construed to imply that these operations are order dependent. Additionally, the structures described herein can be embodied as integrated components or as separate components. For purposes of comparing various embodiments, certain aspects and advantages of these embodiments are described. Not necessarily all such aspects or advantages are achieved by any particular embodiment. Thus, for example, embodiments can be carried out in a manner that achieves or optimizes one advantage or group of advantages without necessarily achieving other advantages or groups of advantages. The methods disclosed herein may include certain actions taken by a practitioner; however, the methods can also include any third-party instruction of those actions, either expressly or by implication. For example, actions such as "deploying a self-expanding filter" include "instructing deployment of a self-expanding filter." The ranges disclosed herein also encompass any and all overlap, sub-ranges, and combinations thereof. Language such as "up to," "at least," "greater than," "less than," "between," and the like includes the number recited. Numbers preceded by a term such as "about" or "approximately" include the recited numbers and should be interpreted based on the circumstances (e.g., as accurate as reasonably possible under the circumstances, for example ±5%, ±10%, ±15%, etc.). For example, "about 7 mm" includes "7 mm." Phrases preceded by a term such as "substantially" include the recited phrase and should be interpreted based on the circumstances (e.g., as much as reasonably possible under the circumstances). For example, "substantially straight" includes "straight."

What is claimed is:

1. A method of inhibiting embolic material from entering cerebral vasculature, the method comprising:
  positioning a guidewire in a left subclavian artery upstream of a left vertebral artery;
  tracking a distal portion of a protection device over the guidewire, the distal portion of the protection device comprising:
    an outer sheath;
    an inner member radially inward of the outer sheath, the inner member comprising a guidewire lumen; and
    a self-expanding filter assembly radially between the outer sheath and the inner member;
  at least one of proximally retracting the outer sheath and distally advancing the self-expanding filter assembly to deploy the self-expanding filter assembly from the outers heath in the left subclavian artery upstream of the left vertebral artery;
  after deploying the self-expanding filter assembly, the inner member prolapses into an aortic arch;
  performing an endovascular procedure, the deployed self-expanding filter assembly inhibiting embolic material from entering cerebral vasculature through the left vertebral artery during the endovascular procedure; and
  after performing the endovascular procedure, withdrawing the self-expanding filter assembly from the left subclavian artery.

2. The method of claim 1, further comprising proximally retracting the inner member out of the aortic arch while the deployed self-expanding filter assembly remains in the left subclavian artery upstream of the left vertebral artery.

3. The method of claim 1, further comprising monitoring arterial pressure using the outer sheath.

4. The method of claim 1, further comprising providing fluid through the outer sheath.

5. The method of claim 1, further comprising positioning a filtering device in an innominate artery and a left common carotid artery, the filtering device inhibiting embolic material from entering cerebral vasculature through a right vertebral artery, a right common carotid artery, and the left common carotid artery during the endovascular procedure.

6. The method of claim 1, wherein the self-expanding filter assembly has a diameter between 7 mm and 12 mm.

7. The method of claim 1, wherein the self-expanding filter assembly has a diameter between 2 mm and 4.5 mm.

8. The method of claim 1, wherein the endovascular procedure being a mitral or aortic valve implantation or replacement.

9. A method of inhibiting embolic material from entering cerebral vasculature, the method comprising:
  positioning a distal portion of a protection device at a location, the location being in the left subclavian artery, the distal portion of the protection device comprising:
    an outer sheath; and
    a self-expanding filter assembly or a self-expanding deflector assembly radially inward of the outer sheath;
    an inner member radially inward of the outer sheath, wherein the inner member comprises a guidewire lumen; and
  deploying the self-expanding filter assembly or self-expanding deflector assembly from the outer sheath at the location, the deployed self-expanding filter assembly or self-expanding deflector assembly inhibiting embolic material from entering cerebral vasculature during an endovascular procedure; and
  after deploying the self-expanding filter assembly or self-expanding deflector assembly, the inner member prolapses into an aortic arch.

10. The method of claim 9, wherein positioning the distal portion of the protection device at the location comprises tracking the distal portion of the protection device over a guidewire.

11. The method of claim 9, further comprising monitoring arterial pressure using at least one of the inner member and the outer sheath.

12. The method of claim 9, wherein the distal portion of the protection device comprises the self-expanding filter assembly.

13. The method of claim 9, wherein the distal portion of the protection device comprises the self-expanding deflector assembly.

14. The method of claim 9, wherein the endovascular procedure comprises atrial valve or mitral valve implantation or replacement.

15. The method of claim 9, wherein deploying the self-expanding filter assembly or self-expanding deflector assembly comprises proximally retracting the outer sheath.

16. The method of claim 9, further comprising proximally retracting the inner member out of the aortic arch while the deployed self-expanding filter assembly or self-expanding deflector assembly remains in the location.

17. The method of claim 9, further comprising positioning a filtering device in an innominate artery and a left common carotid artery, the filtering device inhibiting embolic material from entering cerebral vasculature through a right vertebral artery, a right common carotid artery, and the left common carotid artery during the endovascular procedure.

18. The method of claim 9, wherein the self-expanding filter assembly has a diameter between 7 mm and 12 mm.

19. The method of claim 9, wherein the self-expanding filter assembly has a diameter between 2 mm and 4.5 mm.

20. The method of claim 9, further comprising monitoring arterial pressure.

* * * * *

UNITED STATES PATENT AND TRADEMARK OFFICE
CERTIFICATE OF CORRECTION

PATENT NO.      : 9,566,144 B2
APPLICATION NO. : 14/693763
DATED           : February 14, 2017
INVENTOR(S)     : Cameron Paul Purcell and Daniel Wayne Fifer It is certified that error appears in the above-identified patent and that said Letters Patent is hereby corrected as shown below:

On the Title Page

Item (73) Assignee, Line 1, change "Santa Clara," to --Santa Rosa,--.

In the Claims

At Column 32, Line 4, in Claim 1, change "outers heath" to --outer sheath--.

Signed and Sealed this
Thirtieth Day of May, 2017

Michelle K. Lee
*Director of the United States Patent and Trademark Office*